US009390153B1

(12) United States Patent
Tochilnik

(10) Patent No.: US 9,390,153 B1
(45) Date of Patent: Jul. 12, 2016

(54) USER-CONFIGURABLE RADIOLOGICAL DATA TRANSFORMATION ROUTING AND ARCHIVING ENGINE

(76) Inventor: Dmitriy Tochilnik, San Jose, CA (US)

(*) Notice: Subject to any disclaimer, the term of this patent is extended or adjusted under 35 U.S.C. 154(b) by 0 days.

(21) Appl. No.: 13/385,509

(22) Filed: Feb. 21, 2012

(51) Int. Cl.
*G06F 17/30* (2006.01)

(52) U.S. Cl.
CPC ............................... *G06F 17/30572* (2013.01)

(58) Field of Classification Search
CPC ............................... G06F 17/30; G06F 17/00
See application file for complete search history.

(56) References Cited

U.S. PATENT DOCUMENTS

| | | | | | |
|---|---|---|---|---|---|
| 4,407,294 | A | * | 10/1983 | Vilkomerson | 600/461 |
| 4,575,625 | A | * | 3/1986 | Knowles | 235/462.3 |
| 5,002,561 | A | * | 3/1991 | Fisher | 606/210 |
| 5,179,651 | A | * | 1/1993 | Taaffe et al. | 345/555 |
| 5,220,175 | A | * | 6/1993 | Cole | 250/515.1 |
| 5,237,714 | A | * | 8/1993 | Baron | 5/636 |
| 5,253,653 | A | * | 10/1993 | Daigle et al. | 600/585 |
| 5,325,851 | A | * | 7/1994 | Reynolds et al. | 128/207.16 |
| 5,326,532 | A | * | 7/1994 | Taylor | 422/512 |
| 5,394,455 | A | * | 2/1995 | Roeck et al. | 378/98.3 |
| 5,426,582 | A | * | 6/1995 | Bossaert et al. | 382/274 |
| 5,452,416 | A | * | 9/1995 | Hilton et al. | 715/783 |
| 5,487,290 | A | * | 1/1996 | Miller et al. | 70/303 A |
| 5,564,085 | A | * | 10/1996 | Chen et al. | 455/117 |
| 5,592,237 | A | * | 1/1997 | Greenway et al. | 348/716 |
| 5,653,135 | A | * | 8/1997 | Miller et al. | 70/303 A |
| 5,715,716 | A | * | 2/1998 | Miller et al. | 70/303 A |
| 5,720,194 | A | * | 2/1998 | Miller et al. | 70/303 A |
| 5,740,267 | A | * | 4/1998 | Echerer et al. | 382/132 |
| 5,805,118 | A | * | 9/1998 | Mishra et al. | 345/1.1 |
| 5,807,321 | A | * | 9/1998 | Stoker et al. | 604/65 |
| 5,960,655 | A | * | 10/1999 | Miller et al. | 70/303 A |
| 6,081,267 | A | * | 6/2000 | Stockham et al. | 715/788 |
| 6,210,788 | B1 | * | 4/2001 | Cuypers | 428/316.6 |
| 6,696,973 | B1 | * | 2/2004 | Ritter et al. | 340/539.25 |
| 6,701,343 | B1 | * | 3/2004 | Kenyon | 709/204 |
| 6,751,347 | B2 | * | 6/2004 | Pettigrew et al. | 382/162 |
| 6,757,425 | B2 | * | 6/2004 | Pettigrew et al. | 382/162 |
| 6,898,309 | B2 | * | 5/2005 | Pettigrew et al. | 382/162 |
| 7,219,332 | B2 | * | 5/2007 | Gouge et al. | 717/121 |
| 7,444,390 | B2 | * | 10/2008 | Tadayon et al. | 709/219 |
| 7,624,277 | B1 | * | 11/2009 | Simard et al. | 713/182 |
| 7,630,371 | B2 | * | 12/2009 | Hernandez | G06Q 10/10 370/392 |
| 7,865,358 | B2 | * | 1/2011 | Green et al. | 704/10 |
| 7,899,683 | B2 | * | 3/2011 | Schoenberg | G06F 19/322 600/300 |
| 7,930,636 | B2 | * | 4/2011 | Garbow et al. | 715/713 |
| 7,962,908 | B2 | * | 6/2011 | Gouge et al. | 717/174 |
| 8,000,977 | B2 | * | 8/2011 | Achan | G06Q 10/103 705/2 |
| 8,108,648 | B2 | * | 1/2012 | Srinivasan et al. | 711/170 |
| 8,446,463 | B2 | * | 5/2013 | Fleming et al. | 348/61 |
| 2001/0028735 | A1 | * | 10/2001 | Pettigrew et al. | 382/162 |

(Continued)

OTHER PUBLICATIONS

Corepoint Health, Corepoint Integration Engine, 2009, pp. 1-28.*

(Continued)

*Primary Examiner* — Farhan Syed
(74) *Attorney, Agent, or Firm* — Sheppard Mullin Richter & Hampton LLP

(57) ABSTRACT

A user-configurable radiological data transformation, routing and archiving engine includes a plurality of sub-engines representing algorithms programmed to be processed by a processor, the sub-engines including a user-configurable transformation sub-engine, a user-configurable routing sub-engine, a user-configurable archiving sub-engine and a user-configurable priors puller sub-engine.

12 Claims, 50 Drawing Sheets

(56) References Cited

U.S. PATENT DOCUMENTS

| | | | |
|---|---|---|---|
| 2001/0028736 A1* | 10/2001 | Pettigrew et al. | 382/162 |
| 2001/0028738 A1* | 10/2001 | Pettigrew et al. | 382/162 |
| 2002/0104069 A1* | 8/2002 | Gouge et al. | 717/107 |
| 2005/0165623 A1* | 7/2005 | Landi | G06Q 50/22 705/2 |
| 2006/0052945 A1* | 3/2006 | Rabinowitz | G06F 19/24 702/20 |
| 2007/0064703 A1* | 3/2007 | Hernandez | G06Q 10/10 370/392 |
| 2007/0143215 A1* | 6/2007 | Willems | G06F 19/323 705/51 |
| 2007/0173702 A1* | 7/2007 | Dlugos | G06F 19/3481 600/300 |
| 2008/0046292 A1* | 2/2008 | Myers | G06F 17/30557 705/3 |
| 2008/0288280 A1* | 11/2008 | Belcher | G06F 19/328 705/2 |
| 2009/0063995 A1* | 3/2009 | Baron et al. | 715/753 |
| 2009/0064000 A1* | 3/2009 | Garbow et al. | 715/762 |
| 2009/0132963 A1* | 5/2009 | Morita et al. | 715/834 |
| 2010/0115288 A1* | 5/2010 | Monk | G06F 21/602 713/189 |
| 2011/0119599 A1* | 5/2011 | Klassen et al. | 715/758 |
| 2011/0295873 A1* | 12/2011 | Potter | G06F 19/321 707/769 |
| 2012/0046972 A1* | 2/2012 | Tonti | G06F 19/321 705/3 |
| 2012/0070045 A1* | 3/2012 | Vesper | G06Q 50/22 382/128 |
| 2012/0180071 A1* | 7/2012 | Lesandro et al. | 719/313 |
| 2012/0323593 A1* | 12/2012 | Backhaus | G06F 19/321 705/2 |
| 2013/0060579 A1* | 3/2013 | Yu | G06Q 10/06 705/3 |

OTHER PUBLICATIONS

Eichelberg, Marco, Thomas Aden, Jörg Riesmeier, Asuman Dogac, and Gokce B. Laleci. "A survey and analysis of electronic healthcare record standards." Acm Computing Surveys (Csur) 37, No. 4 (2005):277-315.*

Kimura, Michio, Kazuhiko Ohe, Hiroyuki Yoshihara, Yutaka Ando, Fumiaki Kawamata, Fumito Tsuchiya, Hiroyuki Furukawa et al. "MERIT-9: a patient information exchange guideline using MML, HL7 and DICOM." International journal of medical informatics 51, No. 1 (1998): 59-68.*

* cited by examiner

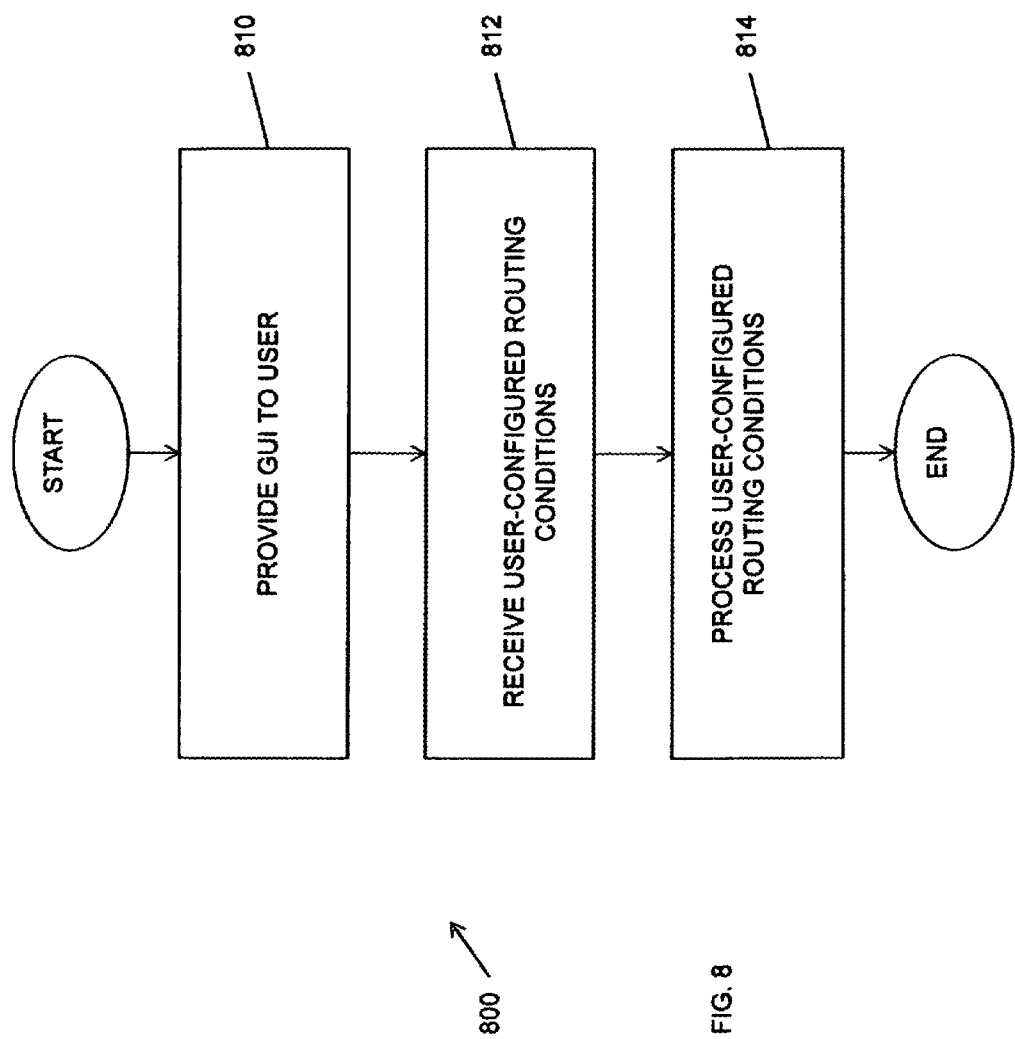

Storage

| | | |
|---|---|---|
| ? | Name: | default — 2510 |
| ? | Description: | default storage — 2520 |
| ? | Path: | /var/dcmsys/storages/default/ — 2530 |
| ? | Storage Durability: | Auto — 2540 |
| ? | Quota Studies: | 0 — 2550 |
| ? | Quota Size: | 0 — 2560 |
| ? | Overwrite Studies: | False — 2570 |
| ? | Overwrite Images: | True — 2580 |

Save  Cancel

Priors puller settings

Puller conditions:

- Name: PRIOR-2-DEMO — 2710
- Description: request CT priors from boxbsec
- Source device: AETitle: * Host: * — 2720
- Local device: AETitle: boxasec Host: * Port: 1043 — 2730, 2740
- Enabled: True — 2750
- Request type: Get/Move — 2752
- Prior fetch limit: 20 (1...N) — 2754
- C-Move dest AE: — 2756
- Other: ((0008,0060) opEquality CT) — 2770
  - And — 2762
  - ((0008,0060) opEquality CT) — 2772
  - Equal — 2764
  - leave empty if you are not sure — 2766

2760

List of prior servers: — 2780 boxbsec:172.16.1.229:1043 — 2782

C-Find request constructor: — 2788

| Operation | Request field | Source field | Modifier Type | Modifier | Mgmt. |
|---|---|---|---|---|---|
| add field | (0010,0020) | (0010,0020) | Copy | | |
| add field | (0008,0060) | (0008,0060) | Copy | | |

2784  2786  2790  2792 add field — 2794

Save  Cancel — 2796

HL7 Workflow

? Event Name: [request_patient_id] — 3210

? Event description: [REQUEST PATIENT ID from TAD] — 3220

? Enabled: [True ▲▼] — 3230

? Tasks: ✓ Click here to add new — 3500

HL7 Condition
    HL7 Transformation
    Route HL7 Message
    Send HL7 Message
    Build Worklist entry
    Export to CSV file
    Build HL7 Message
    Return HL7 Message
    Priors Request
    Submit document to the XDS Repository Service
    Excute Script
    Build Dicom object
    Dicom Condition 3260 — ? Build   Create HL7

3270 — ? Build   Send HL7

3200

Show All   Hide All

[Save]   [Cancel]

FIG. 35

| | |
|---|---|
| Remote AETitle | |
| ⑦ AETitle: | ──3810 |
| ⑦ Host: | |
| ⑦ Port: | |
| ⑦ Enabled: | True ◆ |
| ⑦ Connection Secure Mode: | Nonsecure ◆ ──3820 |
| ⑦ Local Certificate: | RSNA 2011  3830  3840 |
| ⑦ Remote Trusted Certificates: | RSNA 2011 |
| ⑦ TLS Access mode: | Allow any certificate ◆ ──3850 |
| ⑦ Remote Local AE: | |
| ⑦ PDU optimization: | Mode: Default ◆   Size: 131072 ◆ |
| ⑦ Network optimization: | LAN ◆                                    3800 |
| ⑦ Connection timeout | 0                 0 - use default timeout (60 sec) |
| ⑦ Check Connection | No ◆ |
| ⑦ Max Concurrent Connections | 0 - unlimited |
| ⑦ Description: | |
| ⑦ Grouping key: | |
| ⑦ Allowed Incoming Syntaxes | Auto ◆ ──3860 |
| ⑦ Preferred Outgoing Syntaxes | Auto ◆ ──3870 |
| ⑦ Bit preserving mode | False ◆ |
| ⑦ Accept Unknown SOP Classes: | False ◆ |
| ⑦ Storage Commit Mode: | Disable ◆ |
| ⑦ Send MPPS: | Never ◆ |

SOP Class Configuration

SOP Class Tree     Check All    Uncheck All

- ☑ Storage*(84/84 checked)*
- ☑ Worklist and Query/Retrieve*(11/11 checked)*
- ☑ Storage Commitment*(1/1 checked)*
- ☑ MPPS*(3/3 checked)*
- ☑ Verification*(1/1 checked)*
- ☑ Instance Availability Notification*(1/1 checked)*
- ☑ Media Creation Management*(1/1 checked)*
- ☑ SOP Class Relationship Negotiation*(1/1 checked)*
- ☑ UTC Synchronization Frame of Reference (CP 432)*(1/1 checked)*
- ☑ Hanging Protocols*(3/3 checked)*

Enabled transfer syntaxes for [Group: Storage]     Check All    Uncheck All

| | | |
|---|---|---|
| ☑ 1.2.840.10008.1.2.4.90 | JPEG 2000 (Lossless only) | |
| ☑ 1.2.840.10008.1.2.4.91 | JPEG 2000 (Lossless or Lossy) | |
| ☑ 1.2.840.10008.1.2.4.92 | JPEG 2000 Part 2 Multicomponent Image Compression (Lossless only) | |
| ☑ 1.2.840.10008.1.2.4.93 | JPEG 2000 Part 2 Multicomponent Image Compression (Lossless or Lossy) | |
| ☑ 1.2.840.10008.1.2.4.50 | JPEG Baseline | |
| ☑ 1.2.840.10008.1.2.4.51 | JPEG Extended, Process 2+4 | 4200 |
| ☑ 1.2.840.10008.1.2.4.52 | JPEG Extended, Process 3+5 | |
| ☑ 1.2.840.10008.1.2.4.53 | JPEG Spectral Selection, Non-hierarchical, Process 6+8 | |
| ☑ 1.2.840.10008.1.2.4.54 | JPEG Spectral Selection, Non-hierarchical, Process 7+9 | |
| ☑ 1.2.840.10008.1.2.4.55 | JPEG Full Progression, Non-hierarchical, Process 10+12 | |

[Save] [Cancel]

FIG. 42

SOP Class Configuration

SOP Class Tree      Check All    Uncheck All

- ☑ Storage(84/84 checked)
  - ☑ Worklist and Query/Retrieve(11/11 checked)
  - ☑ Storage Commitment(1/1 checked)
  - ☑ MPPS(3/3 checked)
  - ☑ Verification(1/1 checked)
  - ☑ Instance Availability Notification(1/1 checked)
  - ☑ Media Creation Management(1/1 checked)
  - ☑ SOP Class Relationship Negotiation(1/1 checked)
  - ☑ UTC Synchronization Frame of Reference (CP 432)(1/1 checked)
  - ☑ Hanging Protocols(3/3 checked)

Enabled transfer syntaxes for [Group: Storage]      Check All    Uncheck All

| | | |
|---|---|---|
| ☑ 1.2.840.10008.1.2.4.50 | JPEG Baseline | |
| ☑ 1.2.840.10008.1.2.4.51 | JPEG Extended, Process 2+4 | |
| ☑ 1.2.840.10008.1.2.4.52 | JPEG Extended, Process 3+5 | |
| ☑ 1.2.840.10008.1.2.4.53 | JPEG Spectral Selection, Non-hierarchical, Process 6+8 | |
| ☑ 1.2.840.10008.1.2.4.54 | JPEG Spectral Selection, Non-hierarchical, Process 7+9 | |
| ☑ 1.2.840.10008.1.2.4.55 | JPEG Full Progression, Non-hierarchical, Process 10+12 | 4200 |
| ☑ 1.2.840.10008.1.2.4.56 | JPEG Full Progression, Non-hierarchical, Process 11+13 | |
| ☑ 1.2.840.10008.1.2.4.57 | JPEG Lossless, Non-hierarchical, Process 14 | |
| ☑ 1.2.840.10008.1.2.4.58 | JPEG Lossless, Non-hierarchical, Process 15 | |
| ☑ 1.2.840.10008.1.2.4.59 | JPEG Extended, Hierarchical, Process 16+18 | |

[Save] [Cancel]

FIG. 43

SOP Class Configuration

SOP Class Tree  Check All  Uncheck All

- ☑ Storage(84/84 checked)
- ☑ Worklist and Query/Retrieve(11/11 checked)
- ☑ Storage Commitment(1/1 checked)
- ☑ MPPS(3/3 checked)
- ☑ Verification(1/1 checked)
- ☑ Instance Availability Notification(1/1 checked)
- ☑ Media Creation Management(1/1 checked)
- ☑ SOP Class Relationship Negotiation(1/1 checked)
- ☑ UTC Synchronization Frame of Reference (CP 432)(1/1 checked)
- ☑ Hanging Protocols(3/3 checked)

Enabled transfer syntaxes for [Group: Storage]  Check All  Uncheck All

| | | |
|---|---|---|
| ☑ 1.2.840.10008.1.2.4.59 | JPEG Extended, Hierarchical, Process 16+18 | |
| ☑ 1.2.840.10008.1.2.4.60 | JPEG Extended, Hierarchical, Process 17+19 | |
| ☑ 1.2.840.10008.1.2.4.61 | JPEG Spectral Selection, Hierarchical, Process 20+22 | |
| ☑ 1.2.840.10008.1.2.4.62 | JPEG Spectral Selection, Hierarchical, Process 21+23 | |
| ☑ 1.2.840.10008.1.2.4.63 | JPEG Full Progression, Hierarchical, Process 24+26 | |
| ☑ 1.2.840.10008.1.2.4.64 | JPEG Full Progression, Hierarchical, Process 25+27 | 4200 |
| ☑ 1.2.840.10008.1.2.4.65 | JPEG Lossless, Hierarchical, Process 28 | |
| ☑ 1.2.840.10008.1.2.4.66 | JPEG Lossless, Hierarchical, Process 29 | |
| ☑ 1.2.840.10008.1.2.4.70 | JPEG Lossless, Non-hierarchical, 1st Order Prediction | |
| ☑ 1.2.840.10008.1.2.4.80 | JPEG-LS Lossless | |

[Save] [Cancel]

FIG. 44

SOP Class Configuration

SOP Class Tree       <u>Check All</u>   <u>Uncheck All</u>

- ☑ Storage(84/84 checked)
- ☑ Worklist and Query/Retrieve(11/11 checked)
- ☑ Storage Commitment(1/1 checked)
- ☑ MPPS(3/3 checked)
- ☑ Verification(1/1 checked)
- ☑ Instance Availability Notification(1/1 checked)
- ☑ Media Creation Management(1/1 checked)
- ☑ SOP Class Relationship Negotiation(1/1 checked)
- ☑ UTC Synchronization Frame of Reference (CP 432)(1/1 checked)
- ☑ Hanging Protocols(3/3 checked)

Enabled transfer syntaxes for [Group: Storage]      <u>Check All</u>   <u>Uncheck All</u>

| | | |
|---|---|---|
| ☑ 1.2.840.10008.1.2.4.70 | JPEG Lossless, Non-hierarchical, 1st Order Prediction | |
| ☑ 1.2.840.10008.1.2.4.80 | JPEG-LS Lossless | |
| ☑ 1.2.840.10008.1.2.4.81 | JPEG-LS Lossy (Near-lossless) | |
| ☑ 1.2.840.10008.1.2.5 | RLE Lossless | |
| ☑ 1.2.840.10008.1.2.4.100 | MPEG2 Main Profile @ Main Level | |
| ☑ 1.2.840.10008.1.2.1.99 | Deflated Explicit VR Little Endian | 4200 |
| ☑ 1.2.840.10008.1.2.1 | Little Endian Explicit | |
| ☑ 1.2.840.10008.1.2.2 | Big Endian Explicit | |
| ☑ 1.2.840.10008.1.2 | Little Endian Explicit | |

[Save] [Cancel]

FIG. 45

USER-CONFIGURABLE RADIOLOGICAL DATA TRANSFORMATION ROUTING AND ARCHIVING ENGINE

CROSS-REFERENCE TO RELATED APPLICATIONS

Not Applicable

FEDERALLY SPONSORED RESEARCH

Not Applicable

SEQUENCE LISTING OR PROGRAMMING

Not Applicable

BACKGROUND OF THE INVENTION

1. Field of the Invention

The present invention relates to radiological data processing and more particularly to a user-configurable radiological data transformation, routing, and archiving engine.

2. State of the Prior Art

Radiological data processing is a complex field since patient radiological data is stored across multiple facilities. In certain circumstances, doctors and other medical professionals need to be able to automatically pull relevant previous studies from these multiple facilities but encounter the problem that main patient identifiers, patient id for example, can vary from one facility to another. To be useful, patient data must be modified and integrated into a universal worklist where all of the patient's prior studies are accessible. In many cases information contained in structured reports must be read and modified and in certain circumstances, transformation, routing and archiving rules require that data be pulled from a DICOM data object or from DICOM structured reports as well.

Migration of patient radiological images and corresponding data to current standards is another problem and ensuring that all patient radiological data are brought to the same standard is a time-consuming process. Most hospitals hire a consulting company to develop a strategy and custom software for the migration. However PACS, RIS and EMR vendors are usually not willing to cooperate and consequently many hospitals think they have no option but to commit a lot of time and money to having a universal worklist.

Prior art solutions include case by case, customized solutions. The customized approach can be effective but presents clients with a number of challenges. Firstly it can be very difficult to maintain someone else's custom code. Secondly, the client becomes fully dependent upon the provider of its custom solution so changes, even apparently minor ones, can become very expensive. And filially, industry standard protocols such as HL7, DICOM, XDS-I, XML and SNMP are not necessarily used which can result in support issues.

Therefore there is a need for a user-configurable radiological data transmission, routing, and archiving engine that provides for integration of patient radiological studies into a universal worklist, migration of radiological data to current standards, and user-configurable transformation, routing and archiving of radiological data.

SUMMARY OF INVENTION

In accordance with a preferred embodiment of the invention, the user-configurable radiological data transformation, routing and archiving engine uses standard protocols (HL7, DICOM, XDS-I, XML and SNMP) to integrate radiological data (patient studies, orders, and reports for example) across disparate radiology systems (RIS, HIS, EMR) to provide a universal worklist and/or standardized data. The universal worklist provides a user access to all of a patient's prior studies.

In accordance with one aspect of the invention, the user-configurable radiological data transformation, routing and archiving engine provides for migration of patient radiological data to current standards including DICOM, HL7, and XDS-I IHE.

In accordance with another aspect of the invention, the user-configurable radiological data transformation, routing and archiving engine provides a user with configurable transformation of patient radiological data.

In accordance with another aspect of the invention, the user-configurable radiological data transformation, routing and archiving engine provides a user with configurable routing of patient radiological data.

In accordance with another aspect of the invention, the user-configurable radiological data transformation, routing and archiving engine provides a user with configurable archiving of patient radiological data.

In accordance with another aspect of the invention, the user-configurable radiological data transformation, routing and archiving engine provides a user with configurable pulling of patient radiological data.

In accordance with another aspect of the invention, the user-configurable radiological data transformation, routing and archiving engine comprises a software program having computer code processed by a conventional hardware device such as a router or virtual base server.

In accordance with another aspect of the invention, the user-configurable radiological data transformation, routing and archiving engine comprises a plurality of logical sub-engines representing algorithms/routines processed by a conventional device such as a router or virtual base server to provide for user-configurable transformation, routing, archiving and pulling of patient radiological data.

In accordance with another aspect of the invention, the user-configurable radiological data transformation, routing and archiving engine comprises a computer-implemented method having steps processed by a computing device such as a router or virtual base server.

In accordance with another aspect of the invention, the user-configurable radiological data transformation, routing and archiving engine comprises a computer-implemented method having the steps of providing a graphical user interface (GUI) to a user, the GUI providing the user with the ability to configure filter conditions and transformation rules of patient radiological data, receiving the user-configured filter conditions and transformation rules, and processing the user-configured filter conditions and transformation rules in a processor in order to transform patient radiological data.

In accordance with another aspect of the invention, the user-configurable radiological data transformation, routing and archiving engine comprises a computer-implemented method having the steps of providing a graphical user interface (GUI) to a user, the GUI providing the user with the ability to configure routing conditions of patient radiological data, receiving the user-configured routing conditions, and processing the user-configured routing conditions in a processor in order to route patient radiological data.

In accordance with another aspect of the invention, the user-configurable radiological data transformation, routing and archiving engine comprises a computer-implemented method having the steps of providing a graphical user interface (GUI) to a user, the GUI providing the user with the ability to configure conditions for pulling prior patient radiological data, receiving the user-configured conditions for pulling prior patient radiological data, and processing the user-configured conditions for pulling prior patient radiological data in a processor in order to pull prior patient radiological data.

In accordance with another aspect of the invention, the user-configurable radiological data transformation, routing and archiving engine comprises a computer-implemented method having the steps of providing a GUI to a user, the GUI providing the user with means for configuring events in an HL7 workflow, receiving the user-configured events, and processing the user-configured events in a processor in order to transform, route, archive and/or pull patient radiological data.

In accordance with another aspect of the invention, the user-configurable radiological data transformation, routing and archiving engine comprises a computer-implemented method having the steps of providing a GUI to a user, the GUI providing the user with means for configuring a data encryption scheme, receiving the user-configured data encryption scheme, and processing the user-configured data encryption scheme in a processor in order to provide a secure connection between devices.

In accordance with another aspect of the invention, the user-configurable radiological data transformation, routing and archiving engine comprises a computer-implemented method having the steps of providing a GUI to a user, the GUI providing the user with means for configuring a data compression scheme, receiving the user-configured data compression scheme, and processing the user-configured data compression scheme in a processor in order compress patient radiological data.

In accordance with another aspect of the invention, the user-configurable radiological data transformation, routing and archiving engine is communicatively coupled to a network.

There has been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended herein.

In this respect, before explaining at least one embodiment of the invention in detail, it is to be understood that the invention is not limited in its application to the details of design and to the arrangement of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other methods and apparatus for carrying out the several purposes of the present invention. It is important, therefore, that the claims be regarded as including such equivalent methods and apparatus insofar as they do not depart from the spirit and scope of the present invention.

BRIEF DESCRIPTION OF THE DRAWING FIGURES

The present disclosure may be better understood and its numerous features and advantages made apparent to those skilled in the art by referencing the accompanying drawings wherein:

FIG. 8 is a flowchart of a computer-implemented method of providing user-configurable routing conditions;

FIG. 10 is screenshot of a graphical user interface showing a script editor facility;

FIG. 11 is another screenshot of the graphical user interface showing the script editor facility;

FIG. 20 is a screenshot of a graphical user interface that provides for user-configurable radiological data routing;

FIG. 25 is screenshot of a graphical user interface that provides for user-configurable radiological data archiving;

FIG. 27 is a screenshot of a graphical user interface that provides for user-configurable radiological data pulling;

FIG. 35 is a screenshot of the graphical user interface of FIG. 32 showing an HL7 message routing;

FIG. 38 is a screenshot of a graphical user interface that provides for user-configurable encryption schemes;

FIG. 39 is a screenshot of the graphical user interface of FIG. 38 showing a pop-up box of user-selectable certificates;

FIG. 42 is a screenshot of a graphical user interface that provides for user-configurable transfer syntaxes;

FIG. 43 is a screenshot of the graphical user interface of FIG. 42 showing additional transfer syntaxes;

FIG. 44 is a screenshot of the graphical user interface of FIG. 42 showing additional transfer syntaxes; and FIG. 45 is a screenshot of the graphical user interface of FIG. 42 showing additional transfer syntaxes.

DETAILED DESCRIPTION OF A PREFERRED EMBODIMENT

Figure 1:
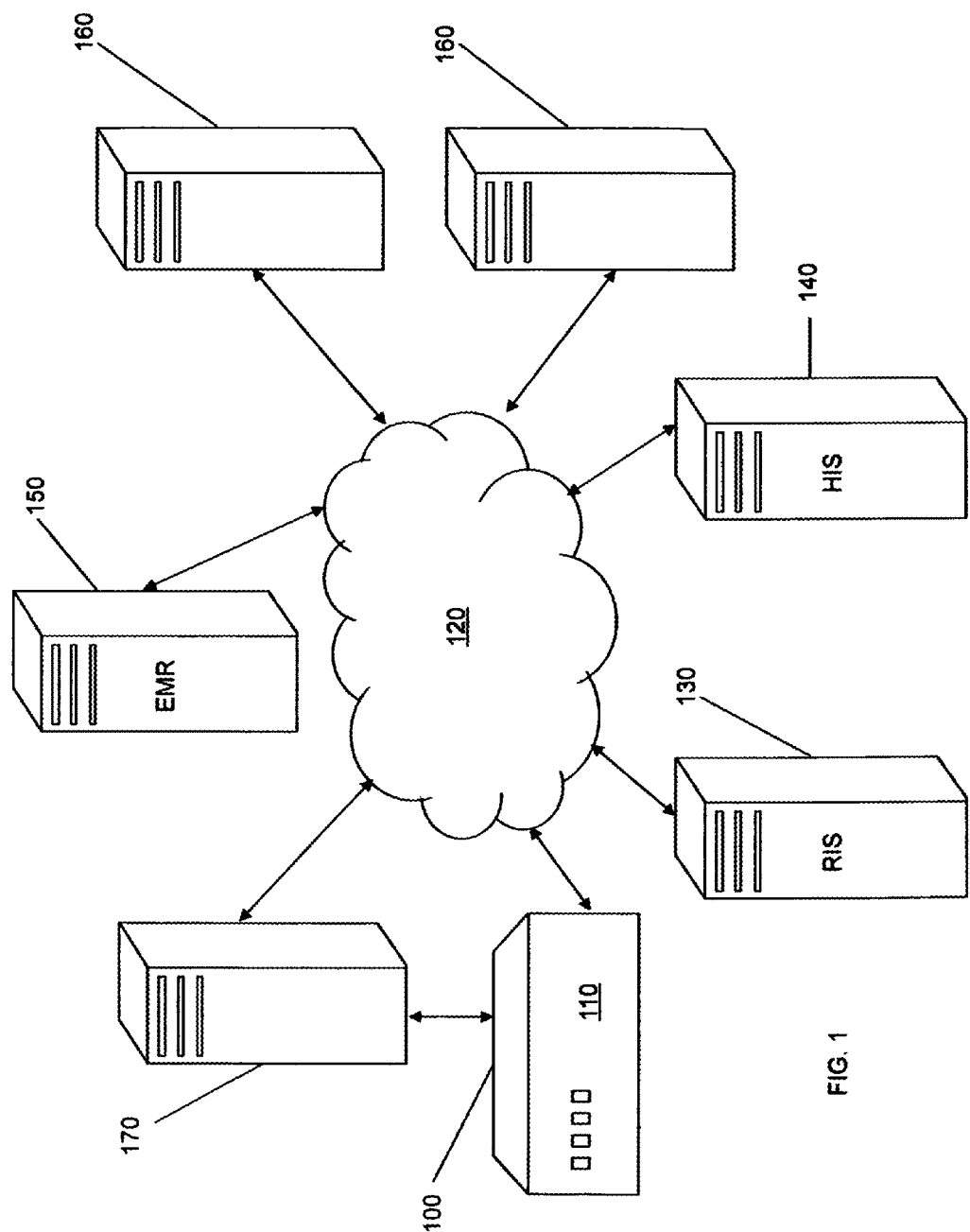
FIG. 1 is a schematic representation of a network environment in which the invention may be practiced.

The invention will now be described in sufficient detail to enable one skilled in the art to make and use the invention. For purposes of brevity, the user-configurable radiological data transformation, routing and archiving engine will hereinafter be referred to as "the engine" and has been given reference number 100 (FIG. 1).

In its broadest aspect, the engine 100 provides a tool and framework that allows a user to configure the transformation, routing, archiving and storage of patient radiological data. The engine 100 also provides of user-configurable encryption and compression of patient radiological data.

More specifically, the engine 100 comprises a software program and computer-implemented method running on a conventional hardware device 110 such as a router or virtual base server (VMWARE, XEN). The hardware device 110 is communicatively connected to the internet 120 and by this means is communicatively coupled to RIS server 130, HIS server 140, EMR server 150 and other servers 160. In one aspect of the invention, the engine 100 is communicatively coupled directly to a server 170 such as a hospital/clinic/radiologist server.

Figure 2:
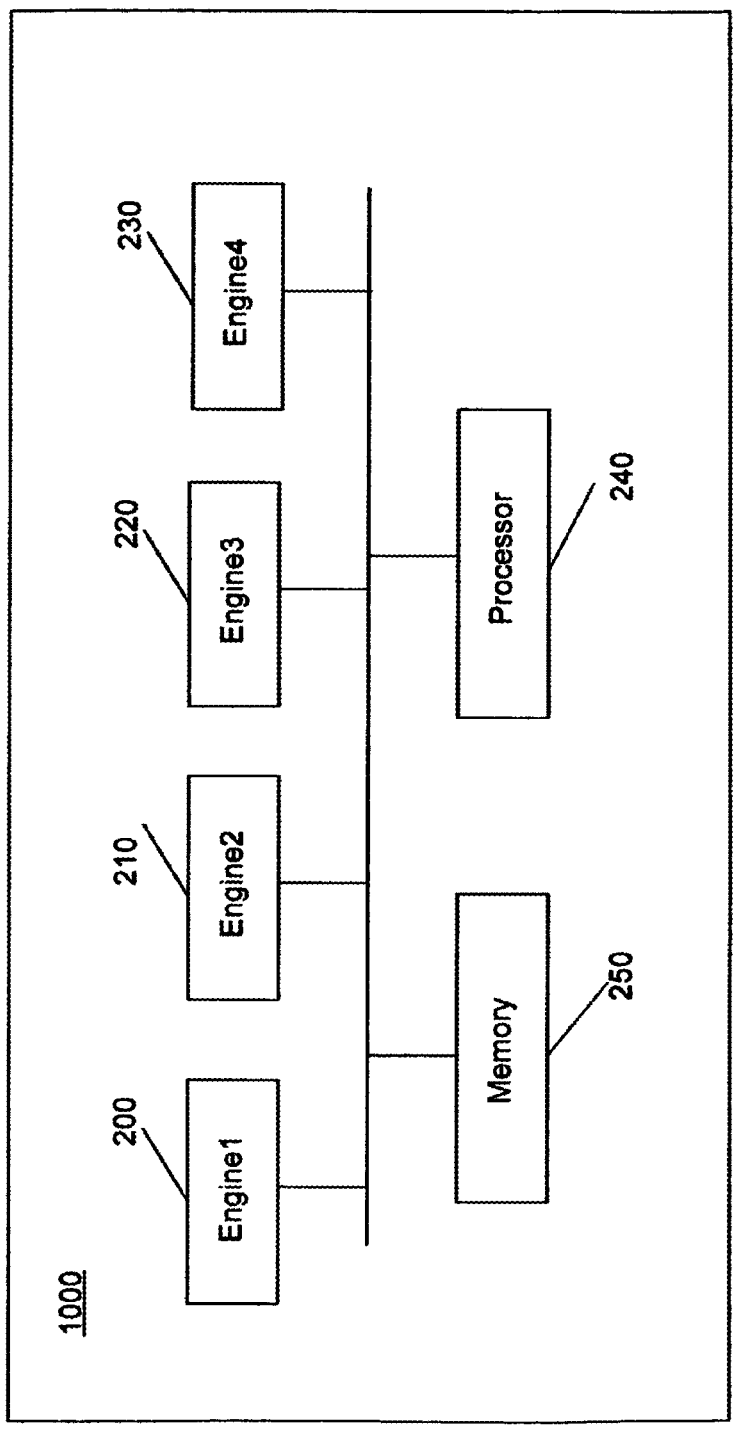
FIG. 2 is a graphical representation of a user-configurable radiological data transformation, routing and archiving engine.

As illustrated in FIG. 2, the engine 100 may be represented by a plurality of sub-engines 200 (engine1), 210 (engine2), 220 (engine3) and 230 (engine4). Sub-engines 200, 210, 220 and 230 are logical representations of algorithms and associated processes/routines stored in a storage medium or memory 250 as computer instructions/code capable of being processed by a processor 240. Other conventional components of the engine 100 such as I/O devices, network interfaces and the like are not shown for simplicity.

Figure 3:
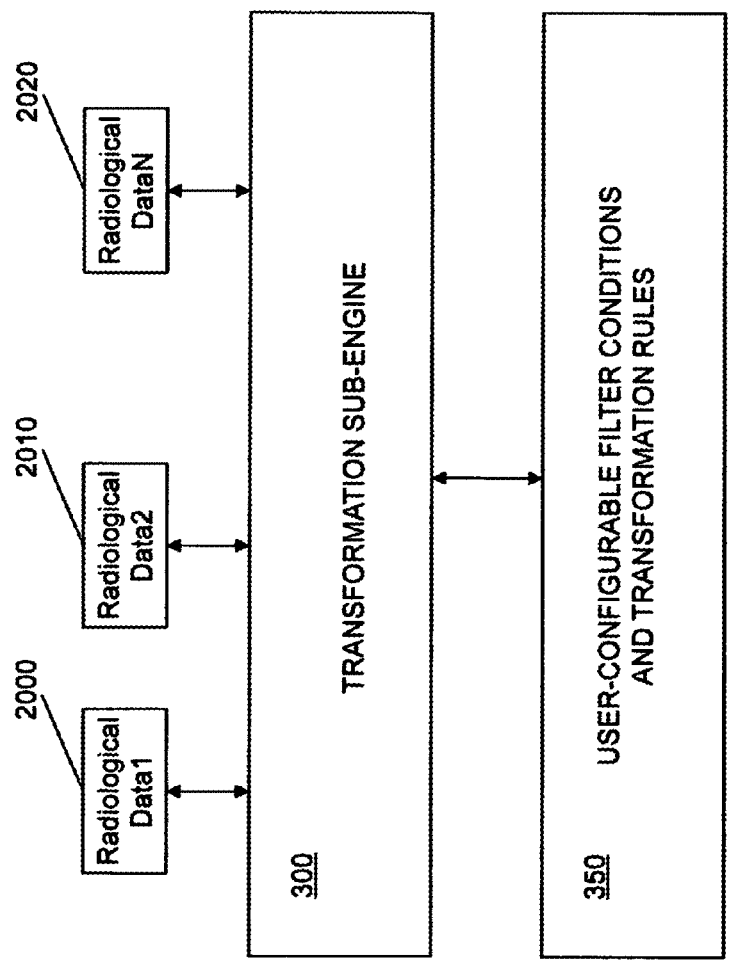
FIG. 3 is a graphical representation of a radiological data transformation sub-engine of the user-configurable radiological data transformation, routing and archiving engine.

A radiological data transformation sub-engine 300 (FIG. 3) uses standard protocols (HL7, DICOM, XML and SNMP) to integrate radiological data 2000 (Radiological Data1), 2010 (Radiological Data2) and 2020 (Radiological DataN) (patient studies, for example) across disparate radiology systems (such as RIS server 130, HIS server 140, and EMR server 150) to provide a universal worklist. The universal worklist provides a user access to all of a patient's prior studies, for example. User-configurable filter conditions and transformation rules 350 provide for transformation of the radiological data 2000, 2010 and 2020 (also referred to as tag morphing) for integration into the universal worklist.

Figure 7:
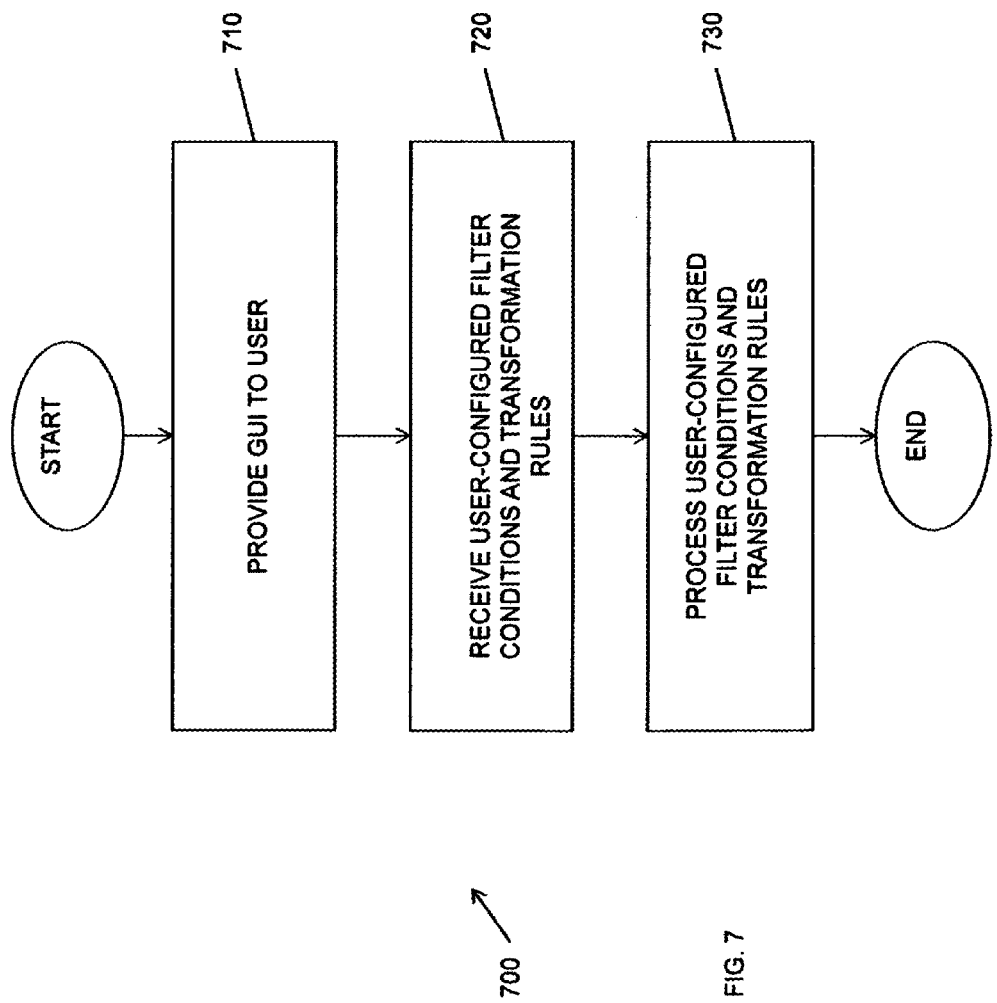
FIG. 7 is a flowchart of a computer-implemented method of providing user-configurable filter conditions and transformation rules.
Figure 8A:
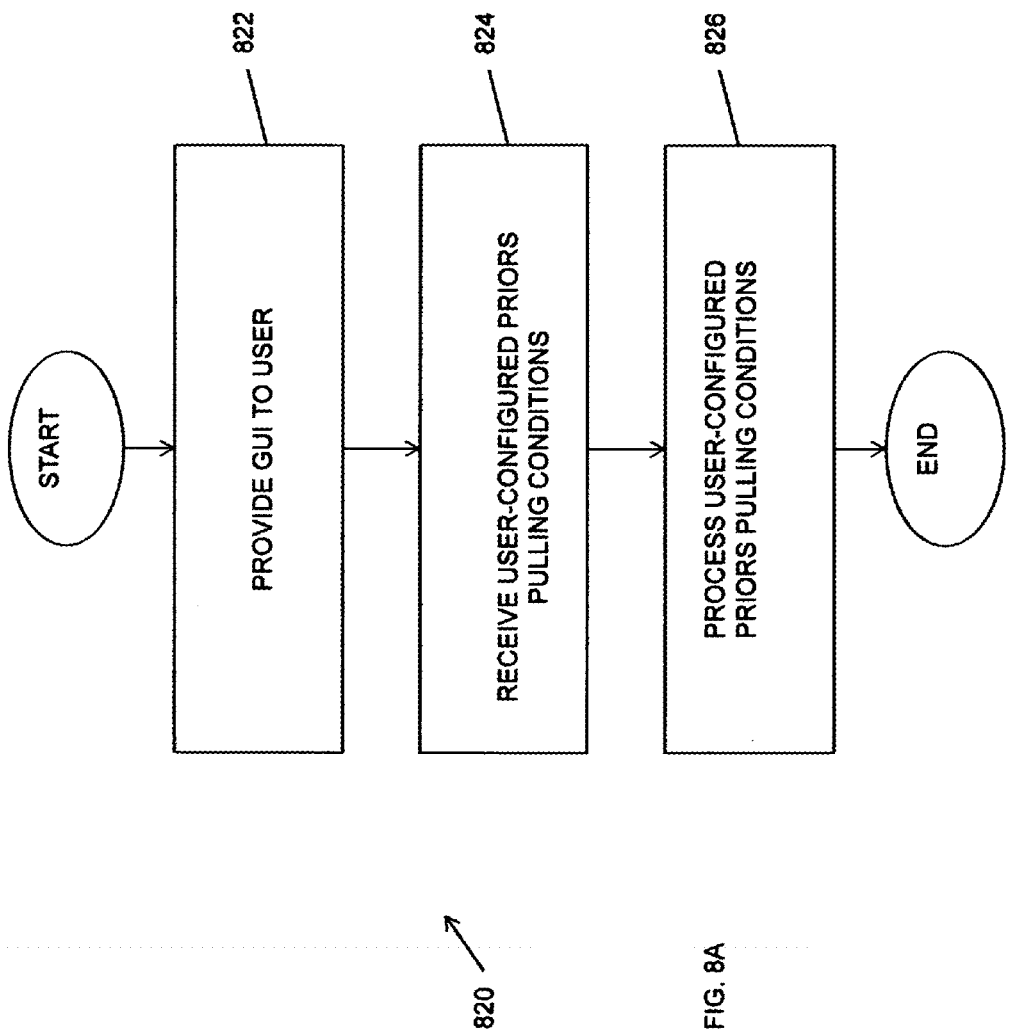
FIG. 8A is a flowchart of a computer-implemented method of providing user-configurable priors pulling conditions.
Figure 8B:
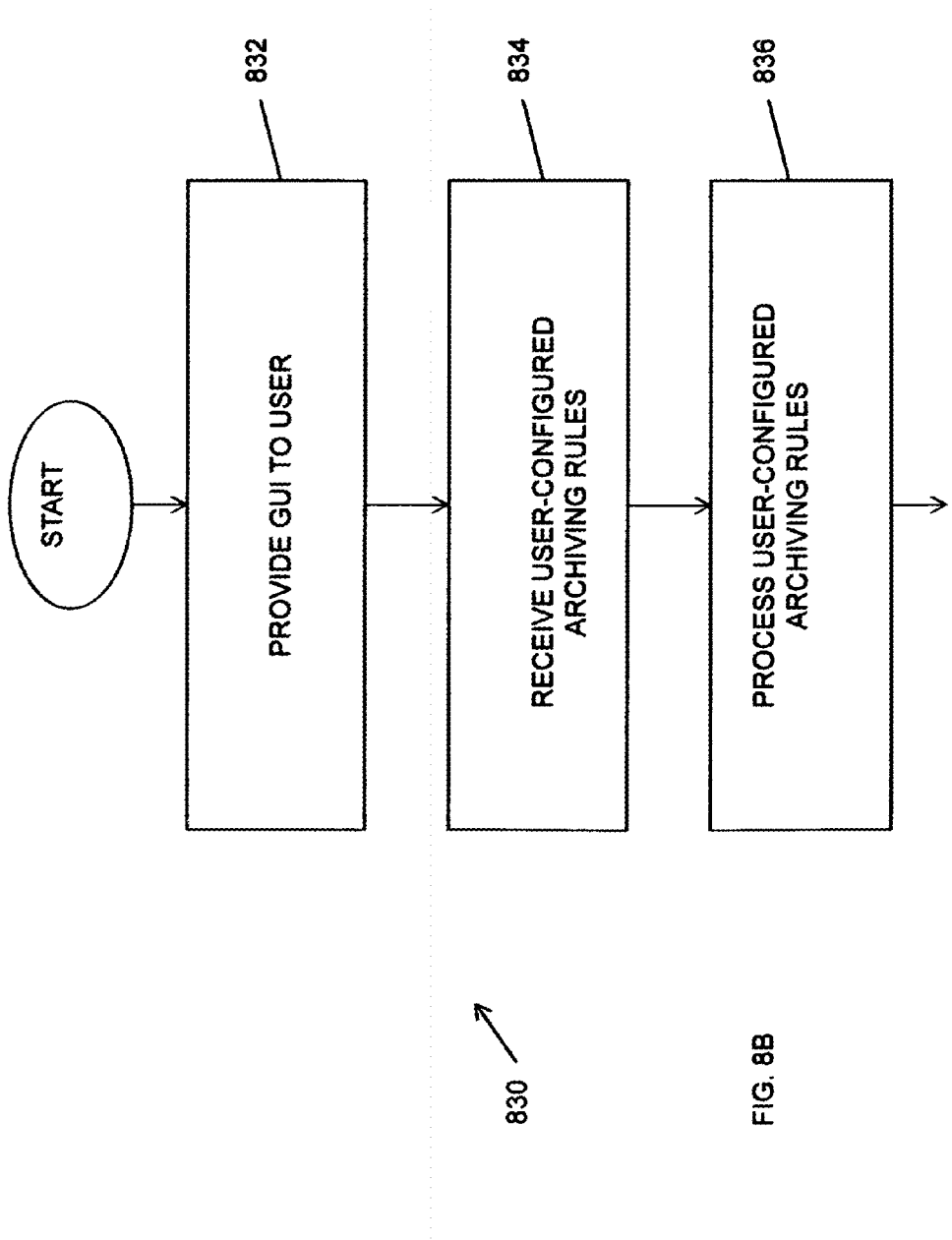
FIG. 8B is a flowchart of a computer-implemented method of providing archiving rules.
Figure 8C:
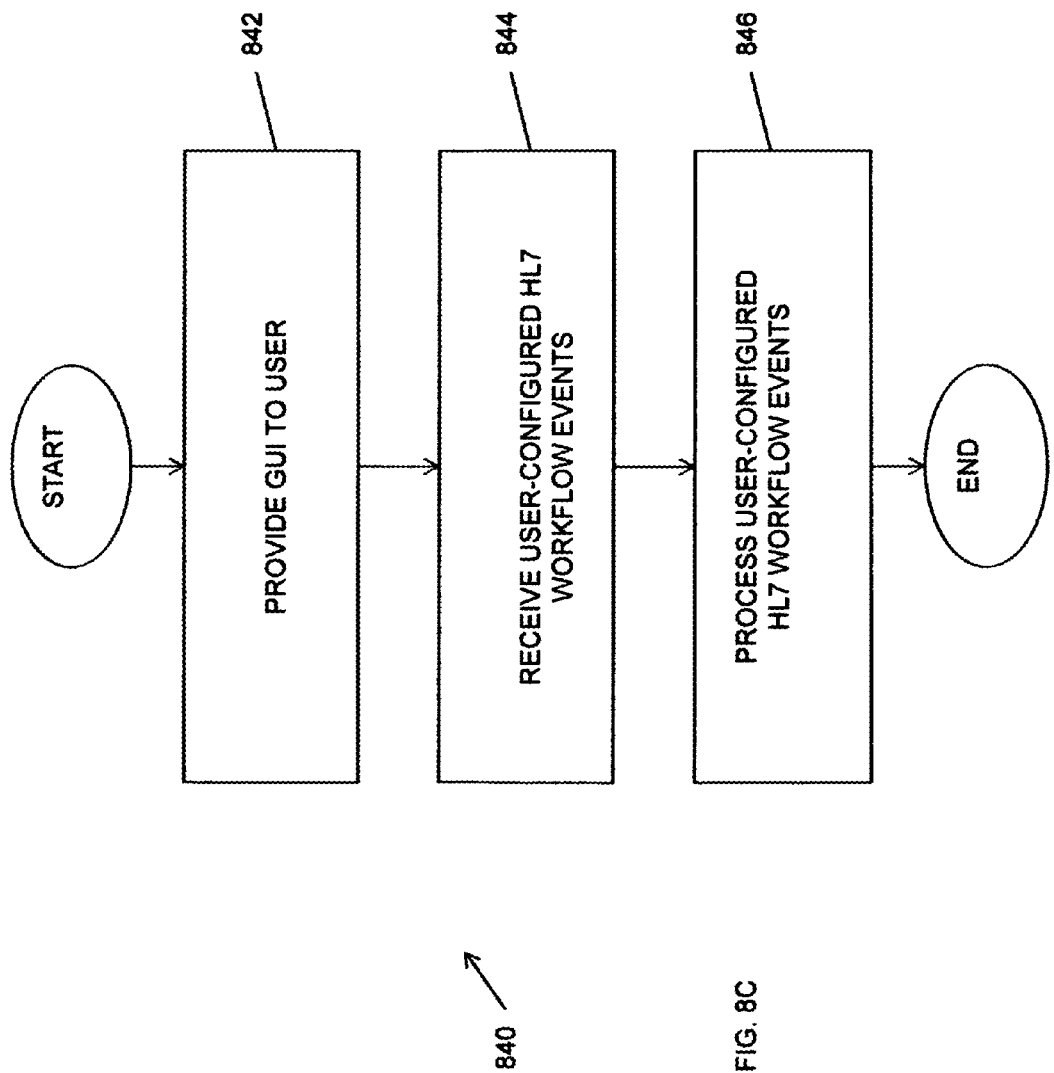
FIG. 8C is a flowchart of a computer-implemented method of providing user-configurable HL7 workflow events.
Figure 8D:
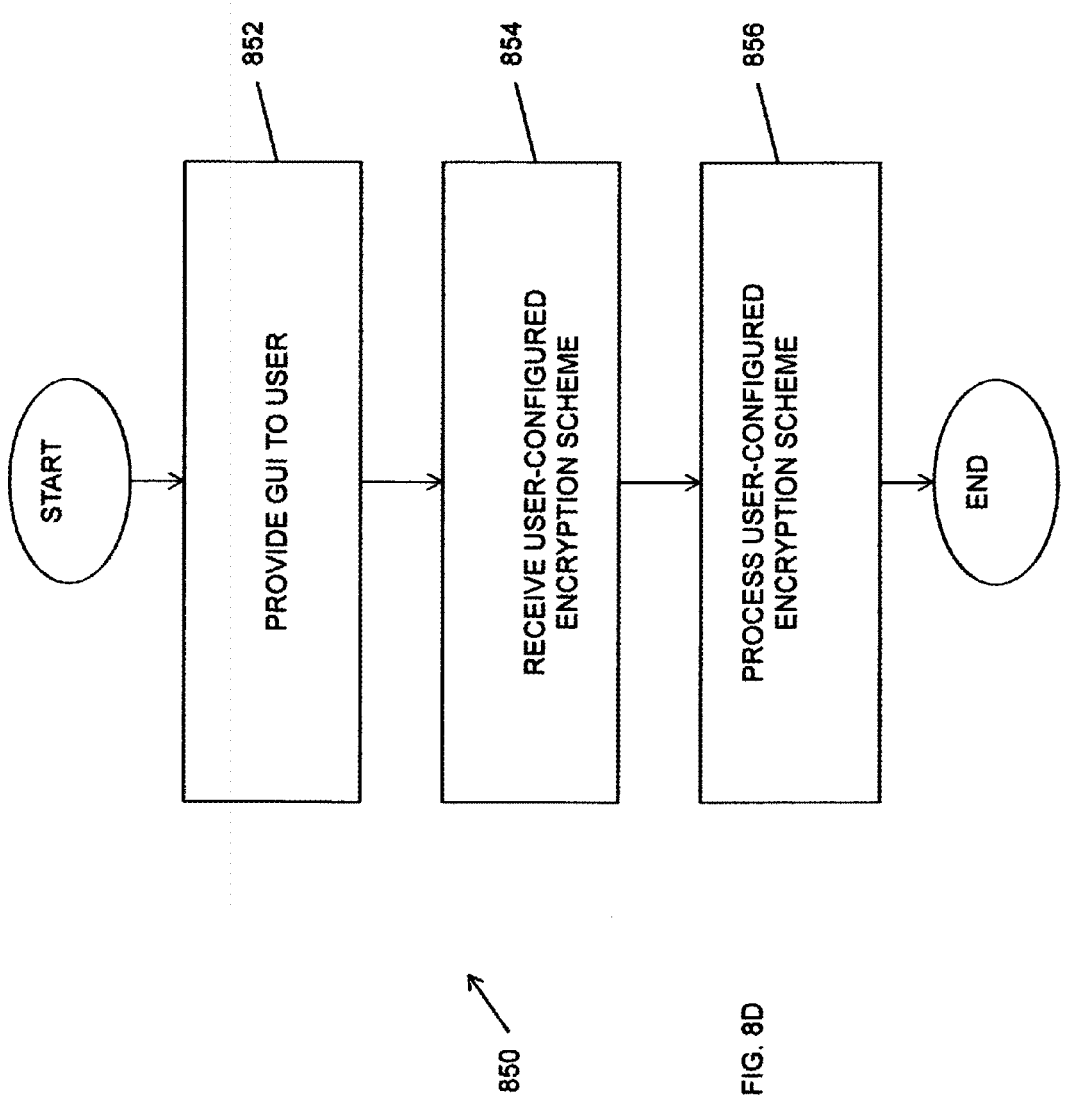
FIG. 8D is a flowchart of a computer-implemented method of providing a user-configurable data encryption scheme.
Figure 8E:
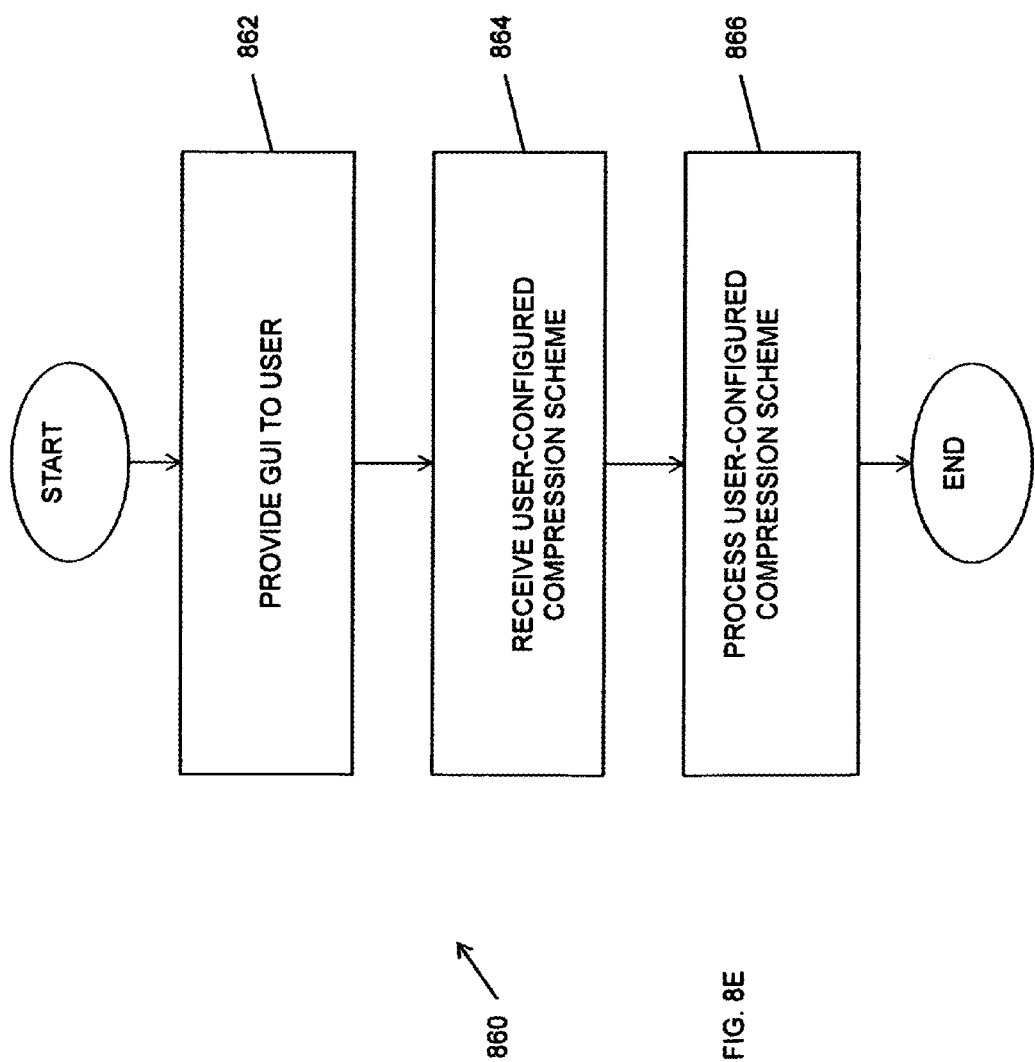
FIG. 8E is a flowchart of a computer-implemented method of providing a user-configurable data compression scheme.

A computer-implemented method 700 (FIG. 7) in accordance with the invention includes the steps of providing 710 a graphical user to the user, receiving 720 user-configured filter conditions and transformation rules, and processing 730 the user-configured filter conditions and transformations rules in a processor to provide the universal worklist.

Figure 9:
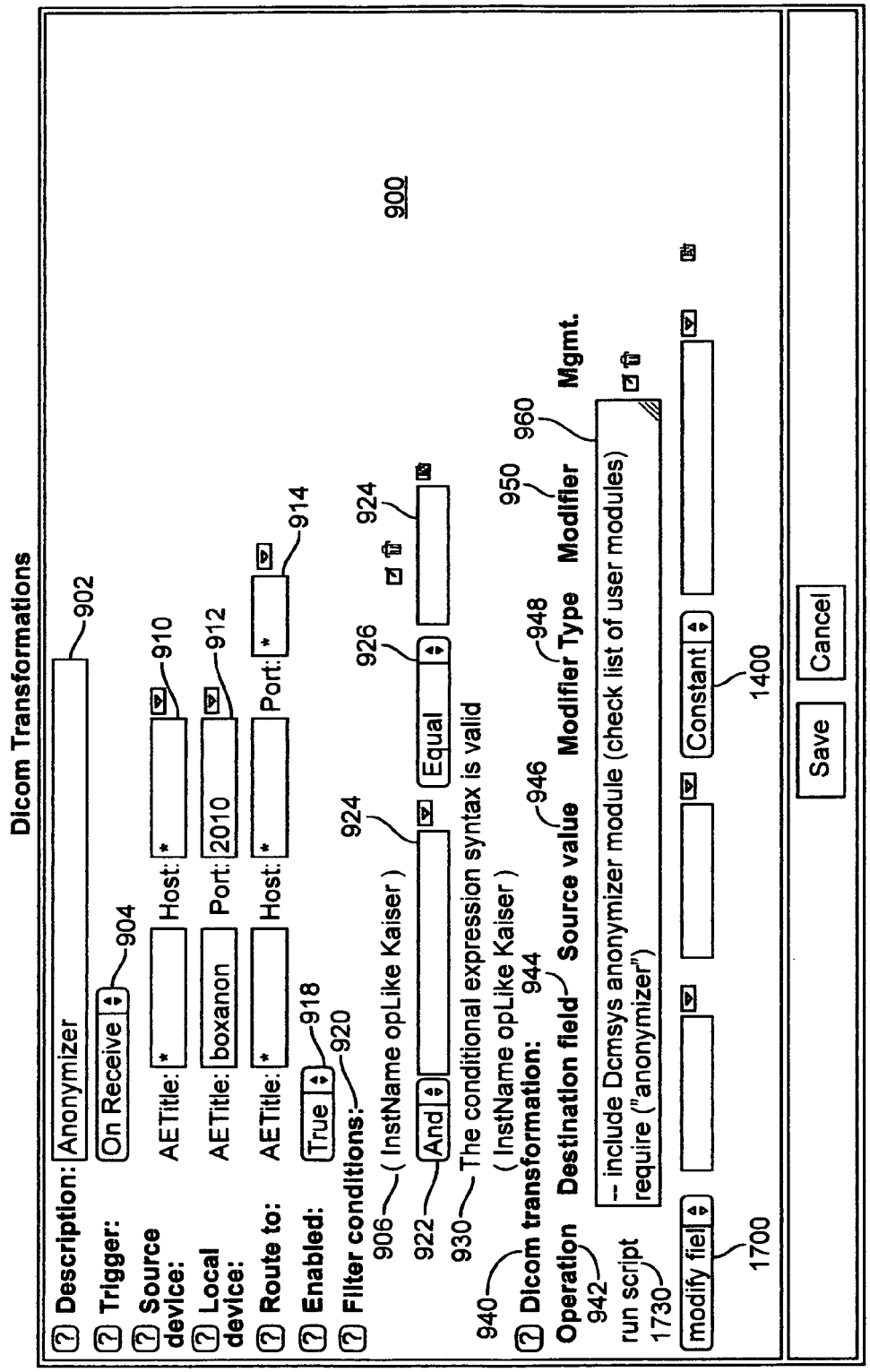
FIG. 9 is a screenshot of a graphical user interface that provides for user-configurable filter conditions and transformation rules.

To provide for user configuration and programming of filter conditions and transformation rules 350, a graphical user interface (GUI) 900 is provided as shown in FIG. 9. The GUI 900 includes a plurality of user-configurable fields including a user-defined Description field 902. A Trigger field 904 is user-configurable to On Receive or On Send. Source device, Local device and Route to fields 910, 912 and 914 respectively are user-configurable to include the application entity title and other information of respective DICOM devices or programs. The DICOM transformation may be enabled (True) or disabled (False) using the Enabled field 918. Filter conditions 920 are user-configurable using the logical operator field 922 (And or Or), the operands fields 924 (comprising DICOM tags 1310 and HL7 Requests 1320 as shown in the pop-up box 1300 of FIG. 13) and the operator field 926. The radiological data transformation sub-engine 300 is operable to provide the user with a confirmation 930 of the syntax of the filter conditions/conditional expression 906.

Figure 14:
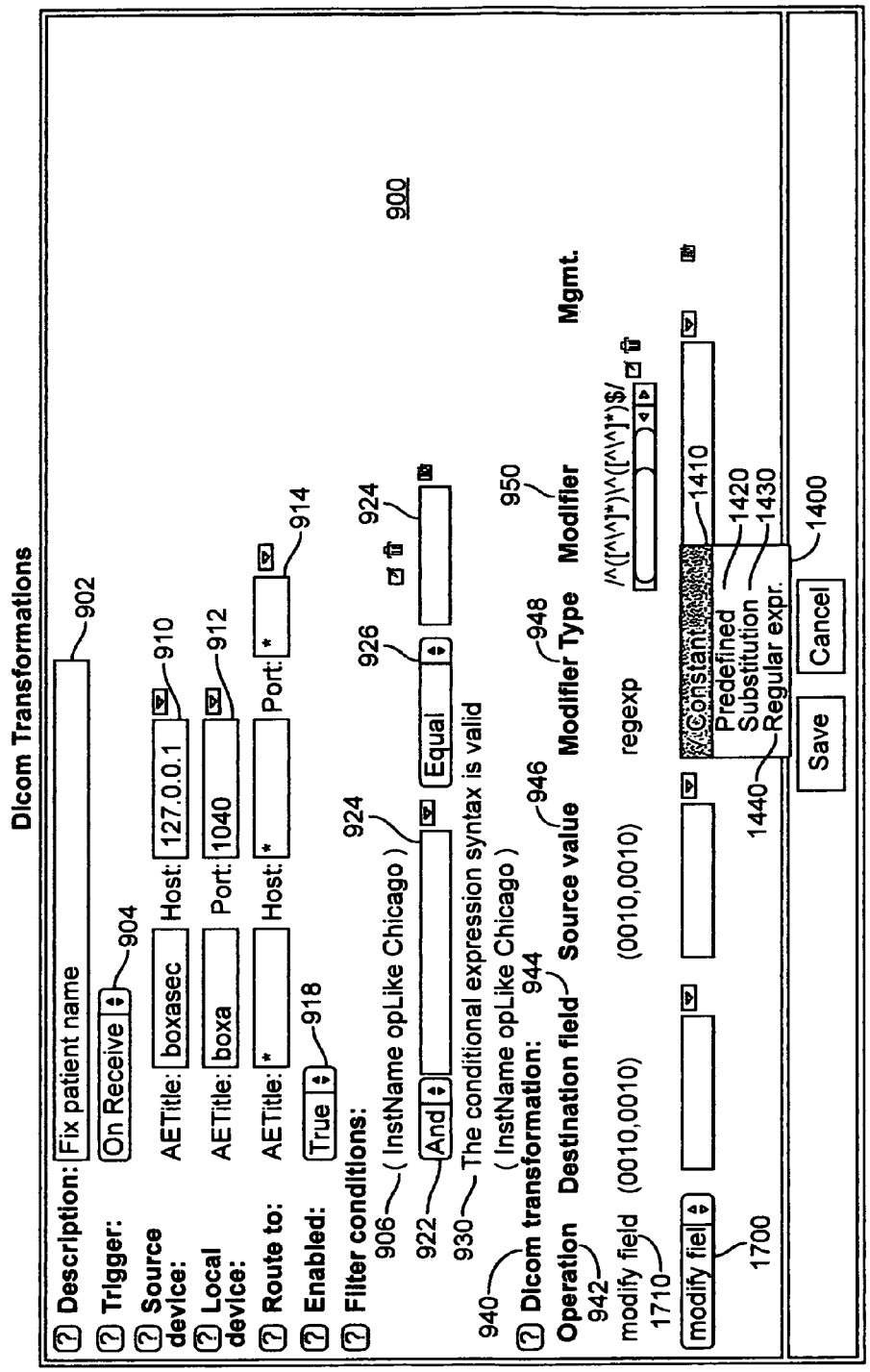
FIG. 14 is a screenshot of the graphical user interface of FIG. 9 showing a pop-up box of user-selectable modifier types.
Figure 17:
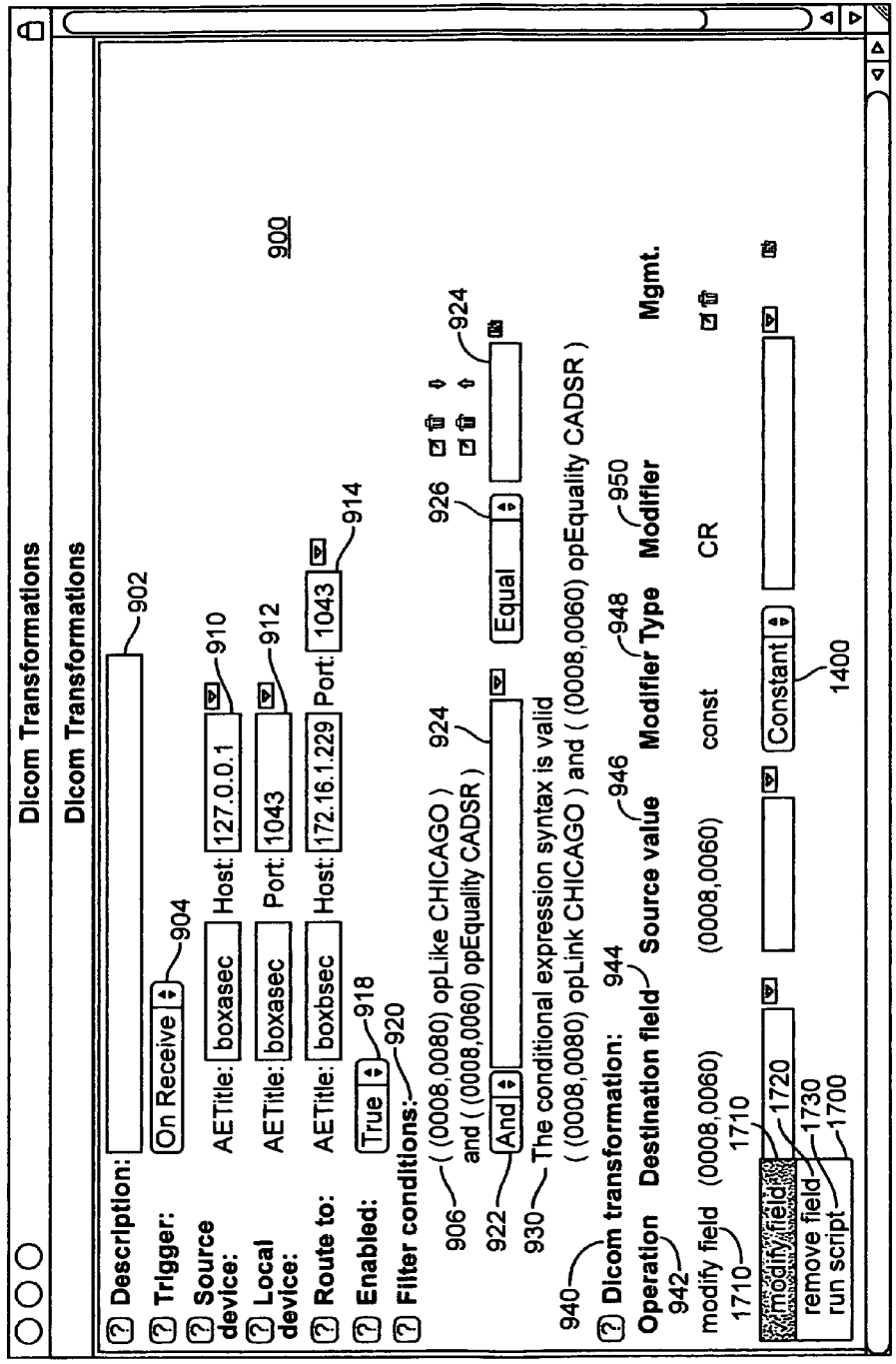
FIG. 17 is a screenshot of the graphical user interface of FIG. 9 that showing a pop-up box of DICOM transformations.

A DICOM transformation field 940 includes the Operation field 942, the Destination field 944, the Source value field 946, the Modifier Type field 948, and the Modifier field 950. The Operation field 942 includes the user-selectable options of modify field 1710, remove field 1720 and run script 1730 as displayed in the pop-up box 1700 in FIG. 17. The Modifier Type field 948 includes the user-selectable options of Constant 1410, Predefined 1420, Substitution 1430 and Regular expr. 1440 as displayed in the pop-up box 1400 in FIG. 14.

Figure 10:
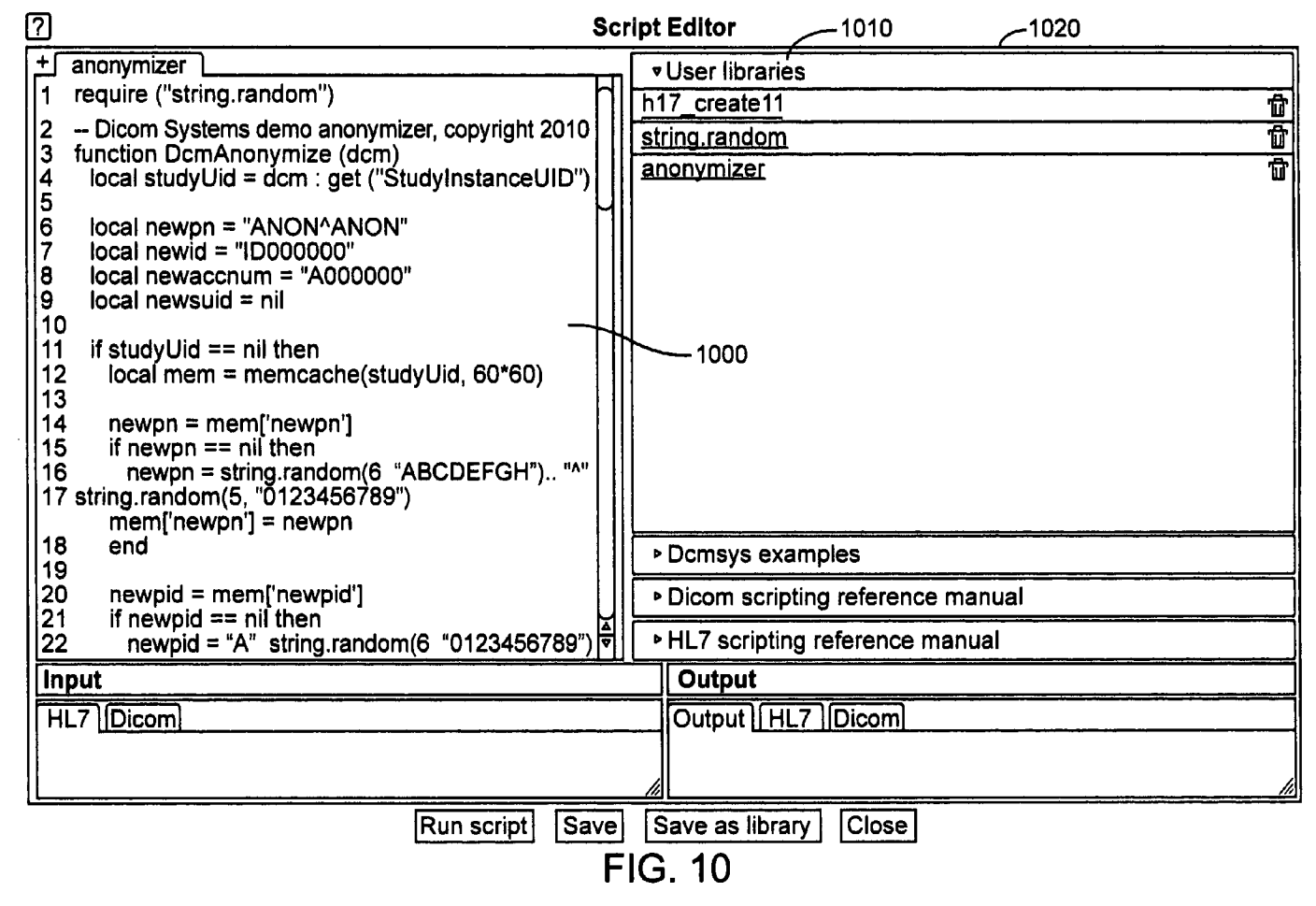
Figure 11:
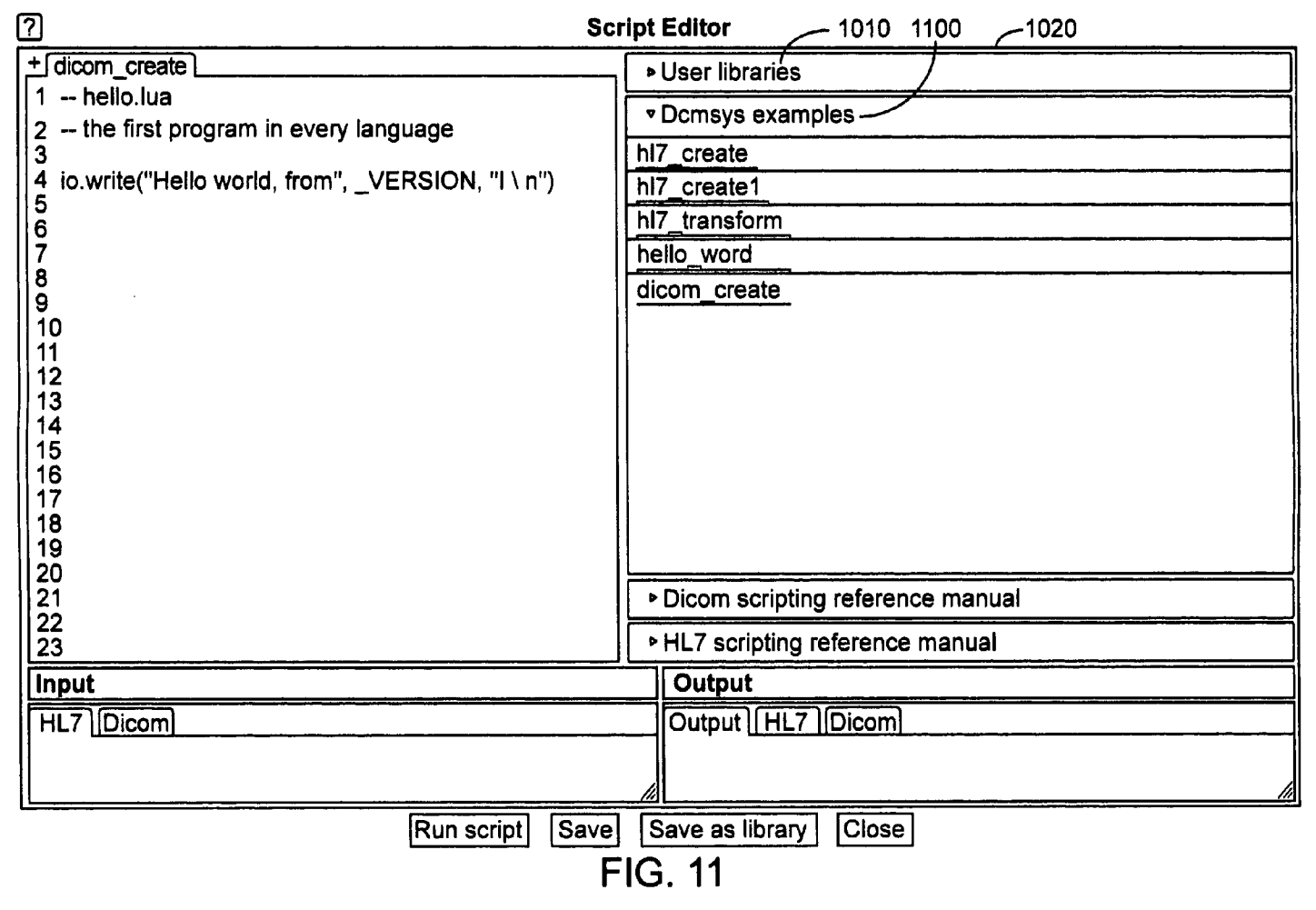

In the GUI 900 of FIG. 9, the run script operation 1730 is selected and comprises the "anonymizer" script 1000 shown in FIG. 10. The "anonymizer" script 1000 is shown as part of a User Library 1010 of a Script Editor GUI 1020. The script editor enables a user to write script in a scripting language such as LUA to provide for user-programmable transformations of the radiological data. Also available to the user are vendor-provided scripts 1030 as shown in FIG. 11.

Figure 12:
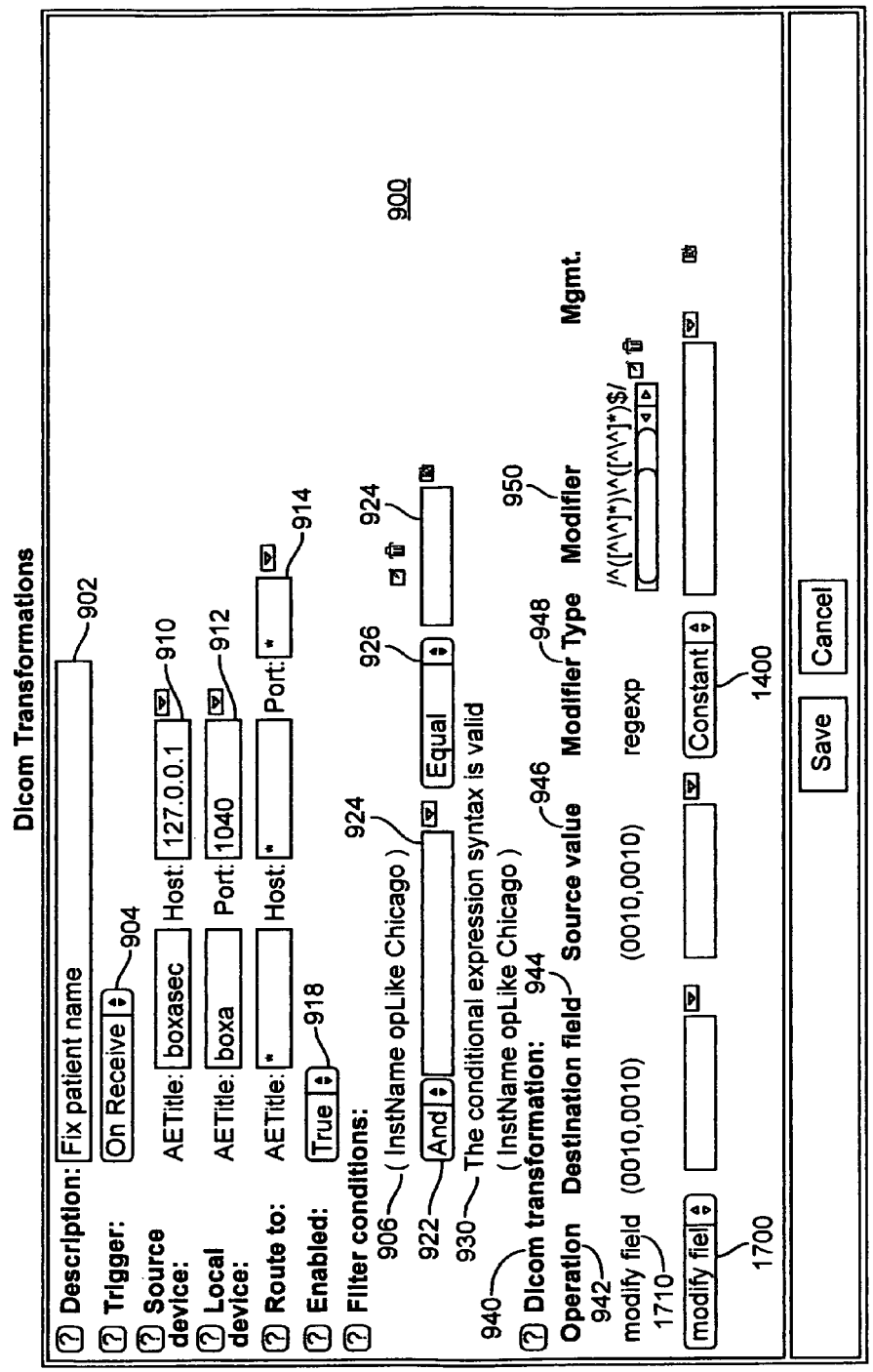
FIG. 12 is another screenshot of the graphical user interface of FIG. 9.

With reference to FIG. 12, the DICOM transformation is entitled "Fix patient name" and the operation modify field 1710 is selected. Values of the Destination field 944 and Source value 946 are shown. In addition the Modifier Type is shown as regexp.

Figure 13:
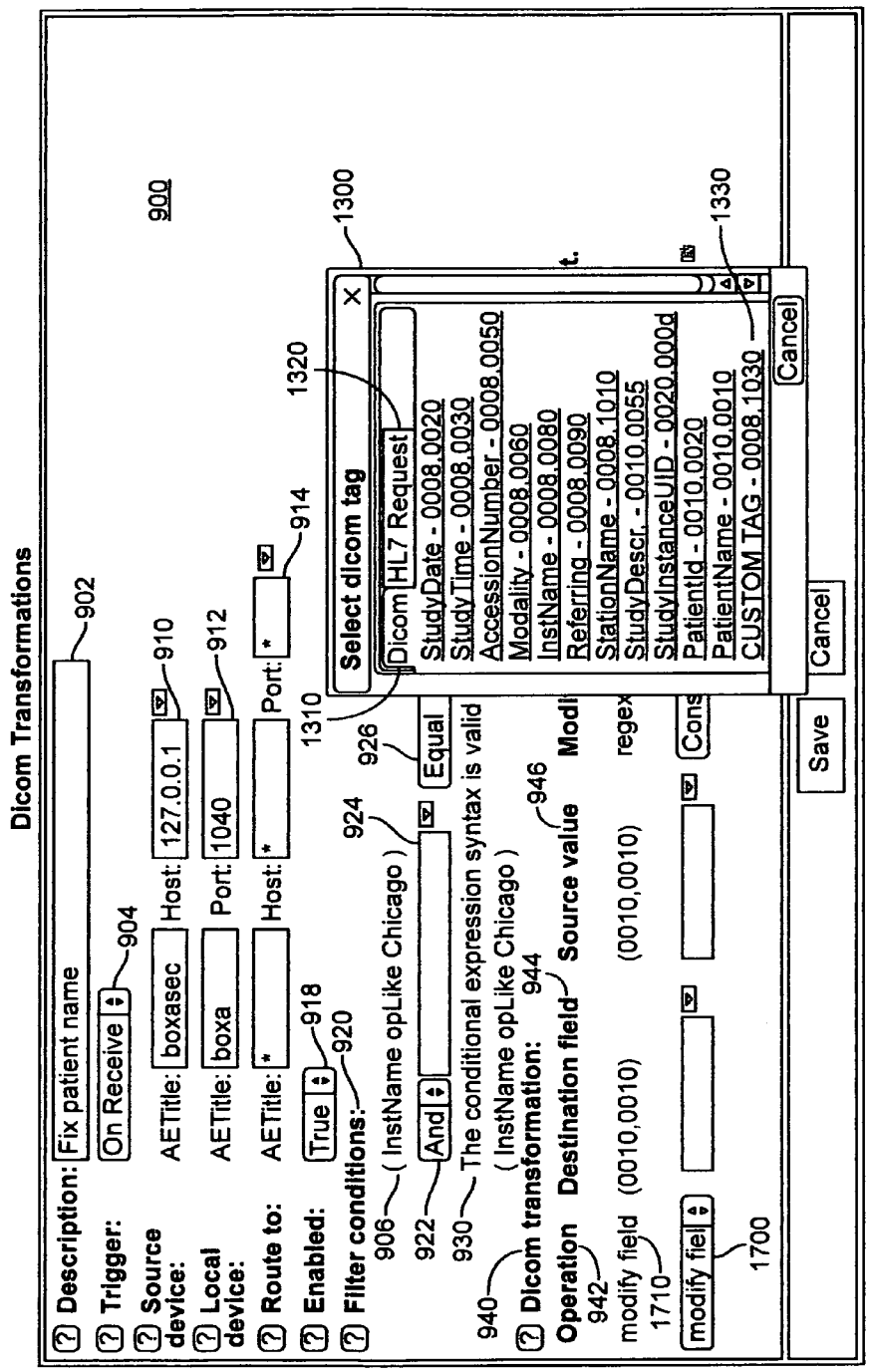
FIG. 13 is a screenshot of the graphical user interface of FIG. 9 showing a pop-up box of user-selectable DICOM tags.

As previously noted, the operands fields 924 are user-selectable from the DICOM tags 1310 displayed in the pop-up box 1300 (FIG. 13). In addition to standard DICOM tags such as StudyDate, StudyTime, AccessionNmber, Modality, InstName, Referring, StationName, StudyDescr, StudyInstanceUID, PatientID, and PatientName, custom tags (such as CUSTOM TAG 1330) are user-configurable. By way of example, a custom tag could include a measurement such as density of a bone or a particular word or words in the radiological data.

Figure 18:
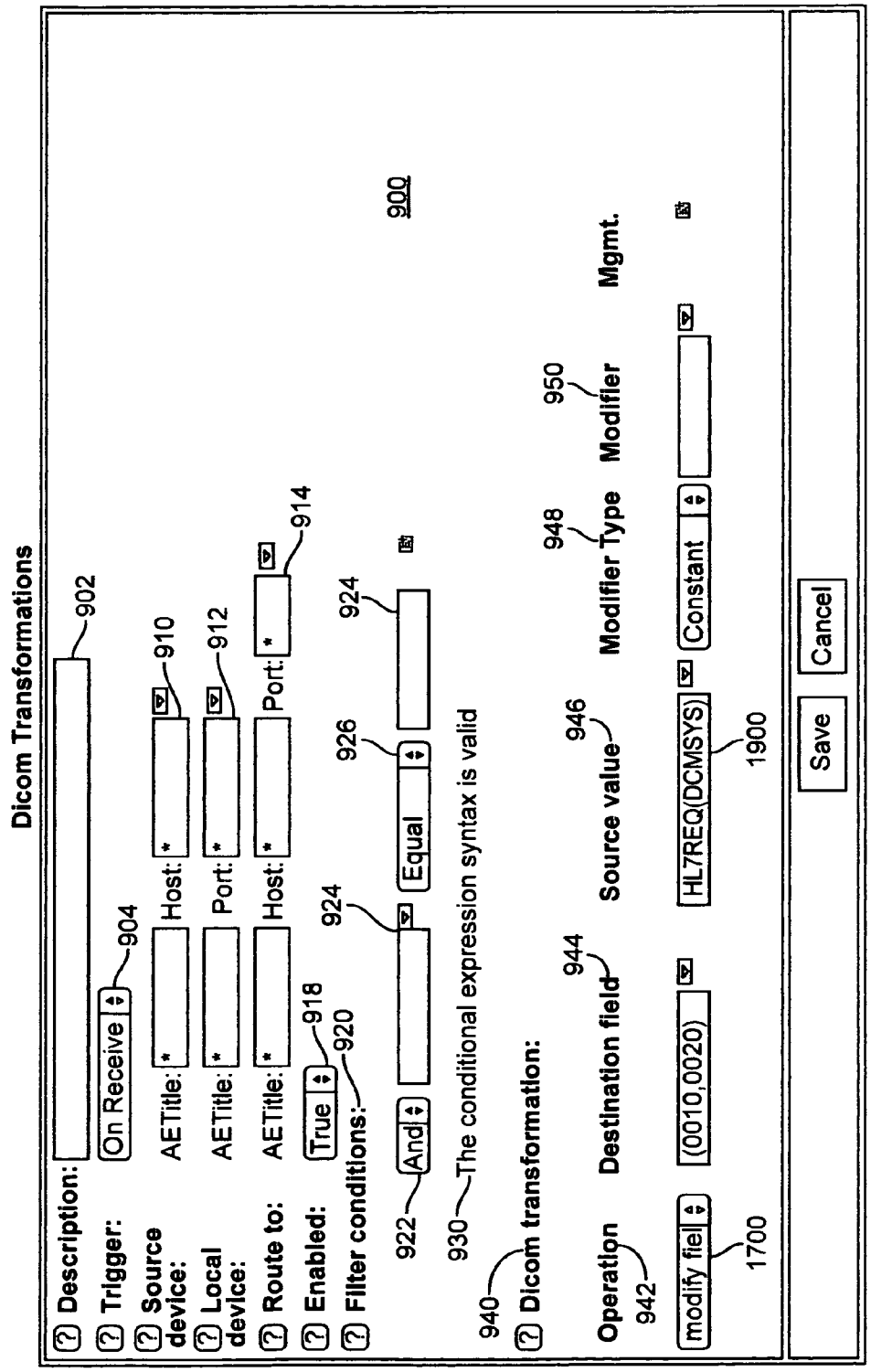
FIG. 18 is a screenshot of the graphical user interface of FIG. 9 showing a user-configurable source value.
Figure 19:
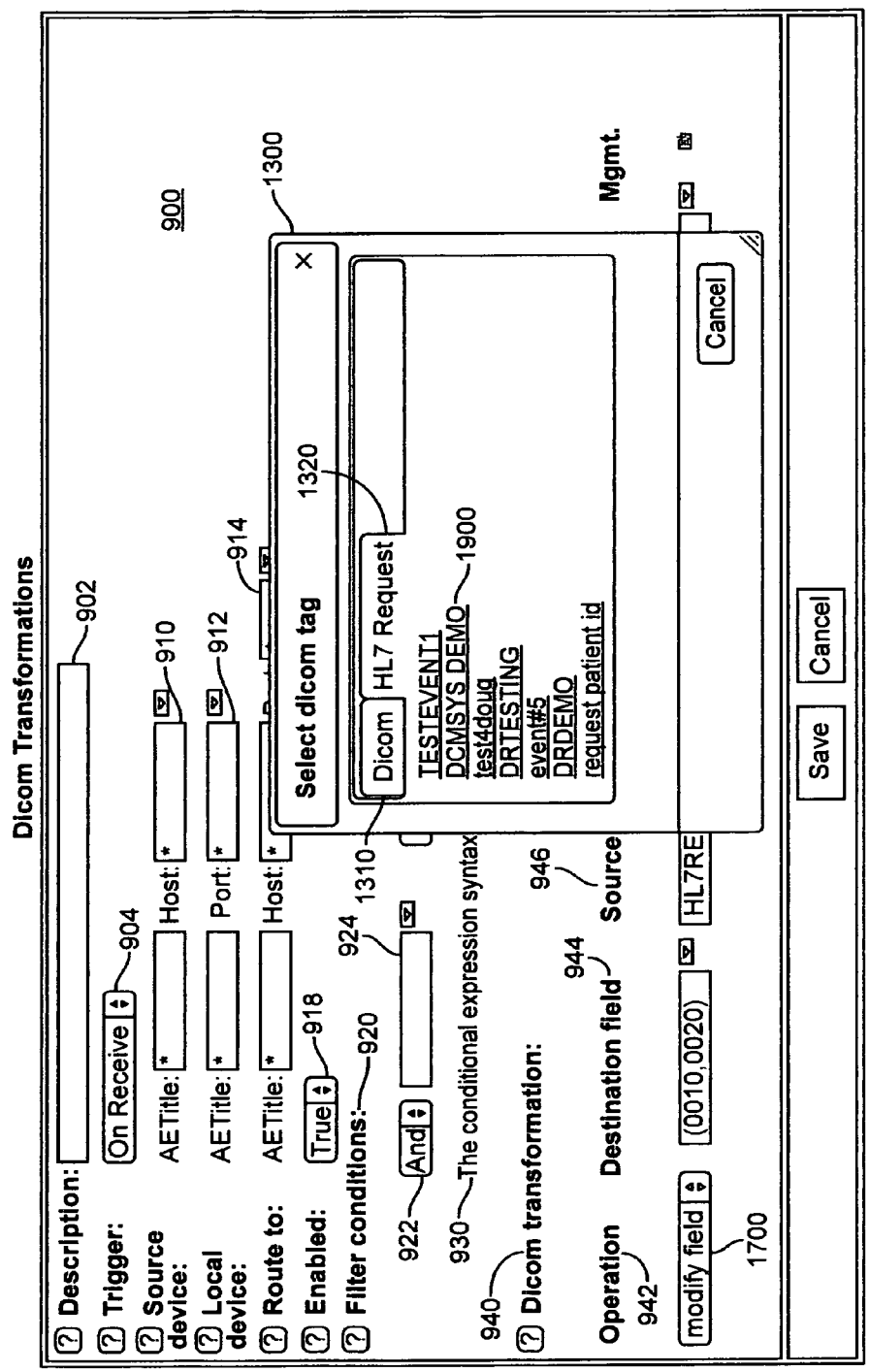
FIG. 19 is a screenshot of the graphical user interface of FIG. 9 showing a pop-up box of user-selectable source values.

The pop-up box 1300 also includes user-configurable HL7 Request 1320 options as shown in FIG. 19. As shown in FIG. 18, the source value 946 is selected to be the HL7 Request DCMSYS DEMO 1900.

Figure 15:
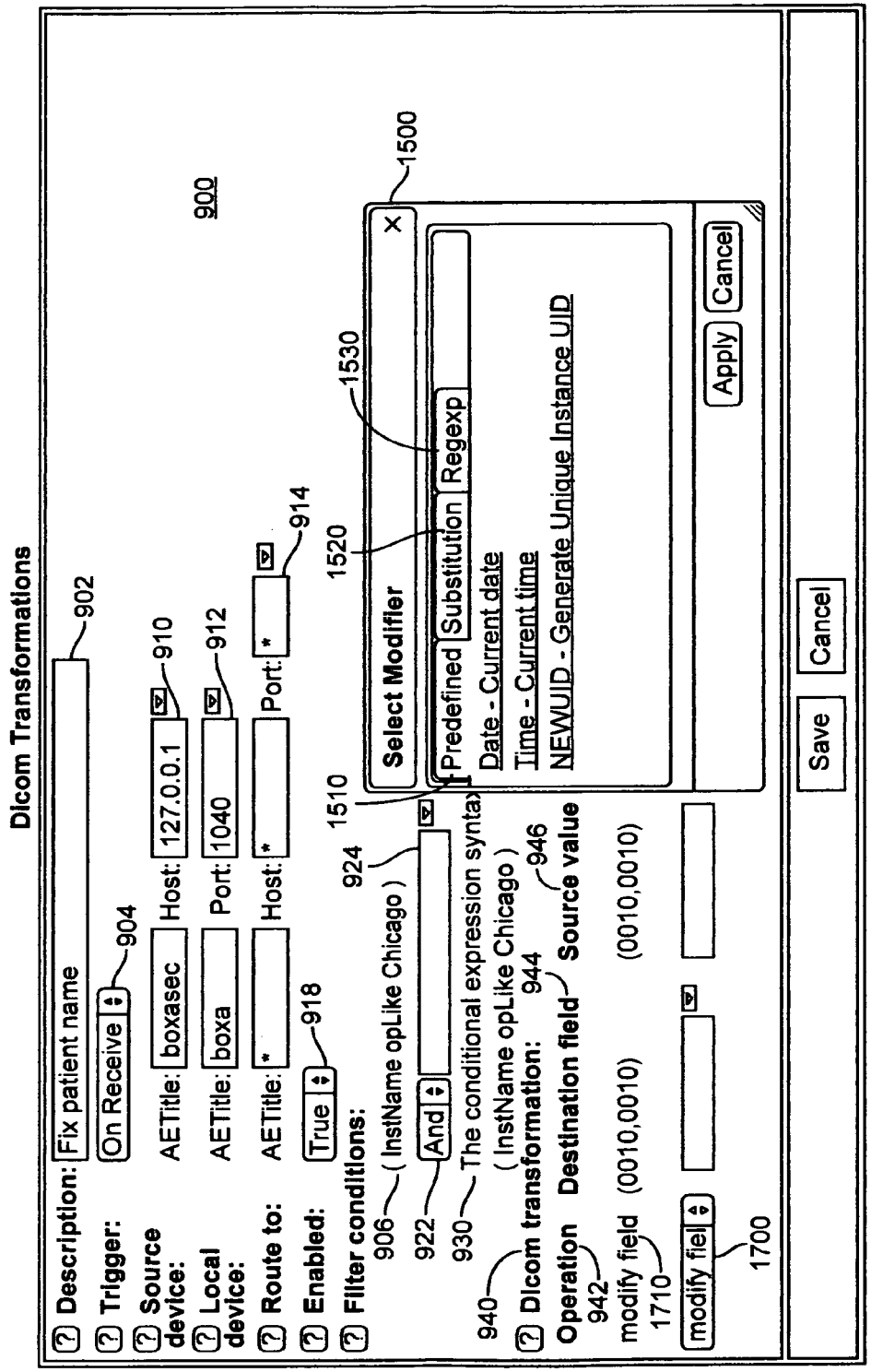
FIG. 15 is a screenshot of the graphical user interface of FIG. 9 showing a pop-up box of user-selectable pre-defined modifiers.
Figure 16:
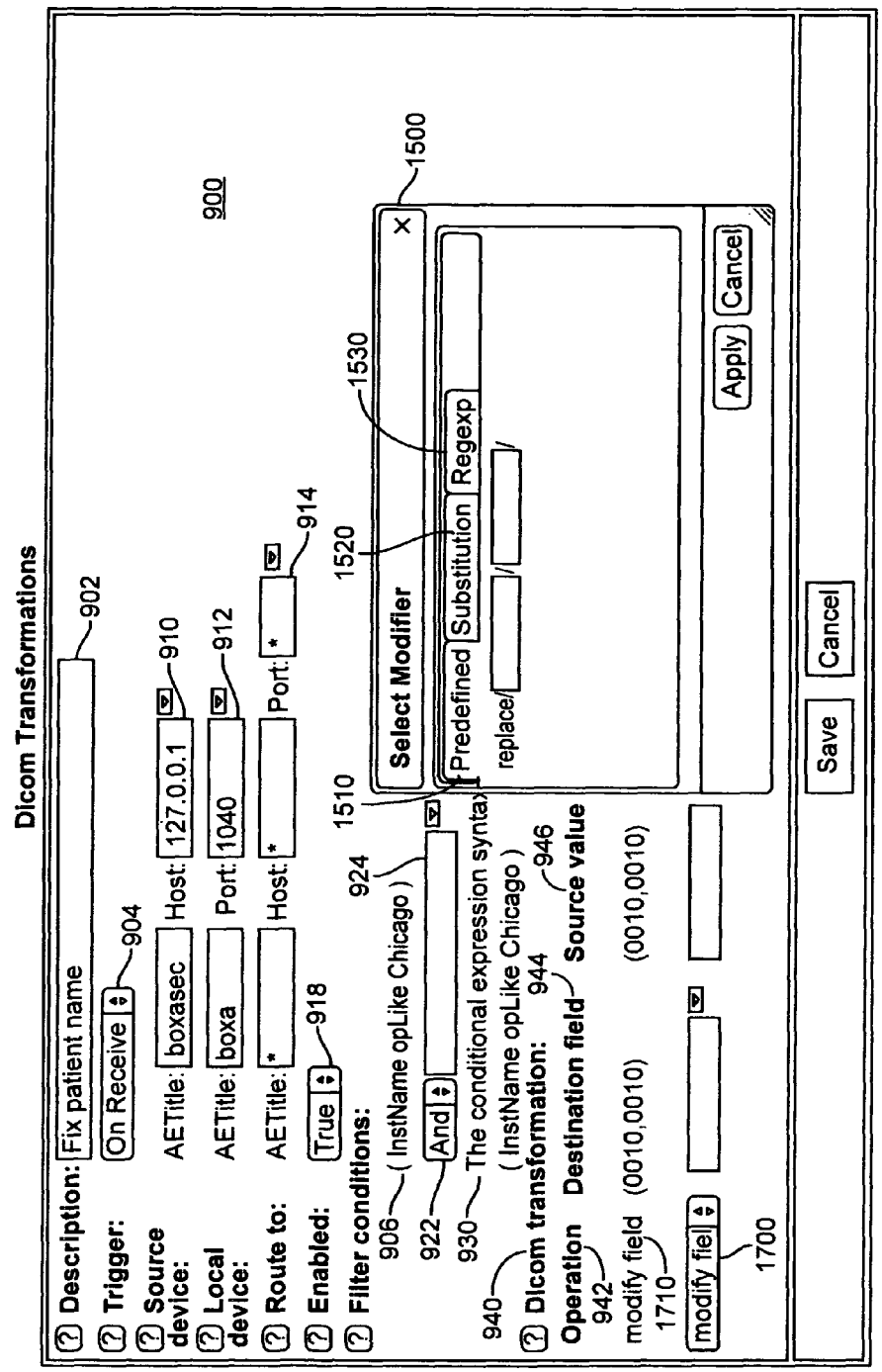
FIG. 16 is a screenshot of the graphical user interface of FIG. 9 showing a pop-up box of user-selectable Regexp modifiers.

Finally, with reference to FIG. 15 and FIG. 16, a Select Modifier pop-up box 1500 includes Predifined modifiers 1510, Substitution modifiers 1520 and Regexp modifiers 1530.

Figure 4:
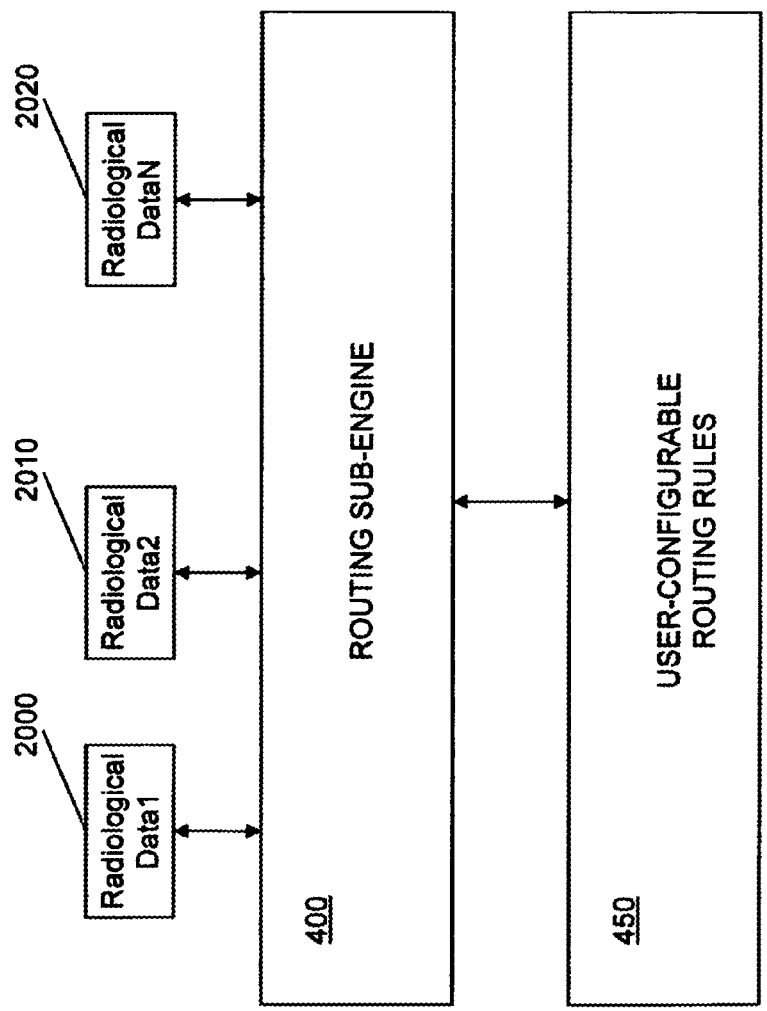
FIG. 4 is a graphical representation of a radiological data routing sub-engine of the user-configurable radiological data transformation, routing and archiving engine.

A radiological data routing sub-engine 400 (FIG. 4) uses standard protocols (HL7, DICOM, XML and SNMP) to route radiological data 2000 (Radiological Data1), 2010 (Radiological Data2) and 2020 (Radiological DataN) (patient studies, for example) from disparate radiology systems (such as RIS server 130, HIS server 140, and EMR server 150) to provide for migration to a common standard. User-configurable routing rules 450 provide for routing of the radiological data 2000, 2010 and 2020.

A computer-implemented method 800 (FIG. 8) in accordance with the invention includes the steps of providing 810 a graphical user to the user, receiving 812 user-configured routing conditions, and processing 814 the user-configured routing conditions in a processor to provide for standardized routing of patient radiological data.

Figure 20:
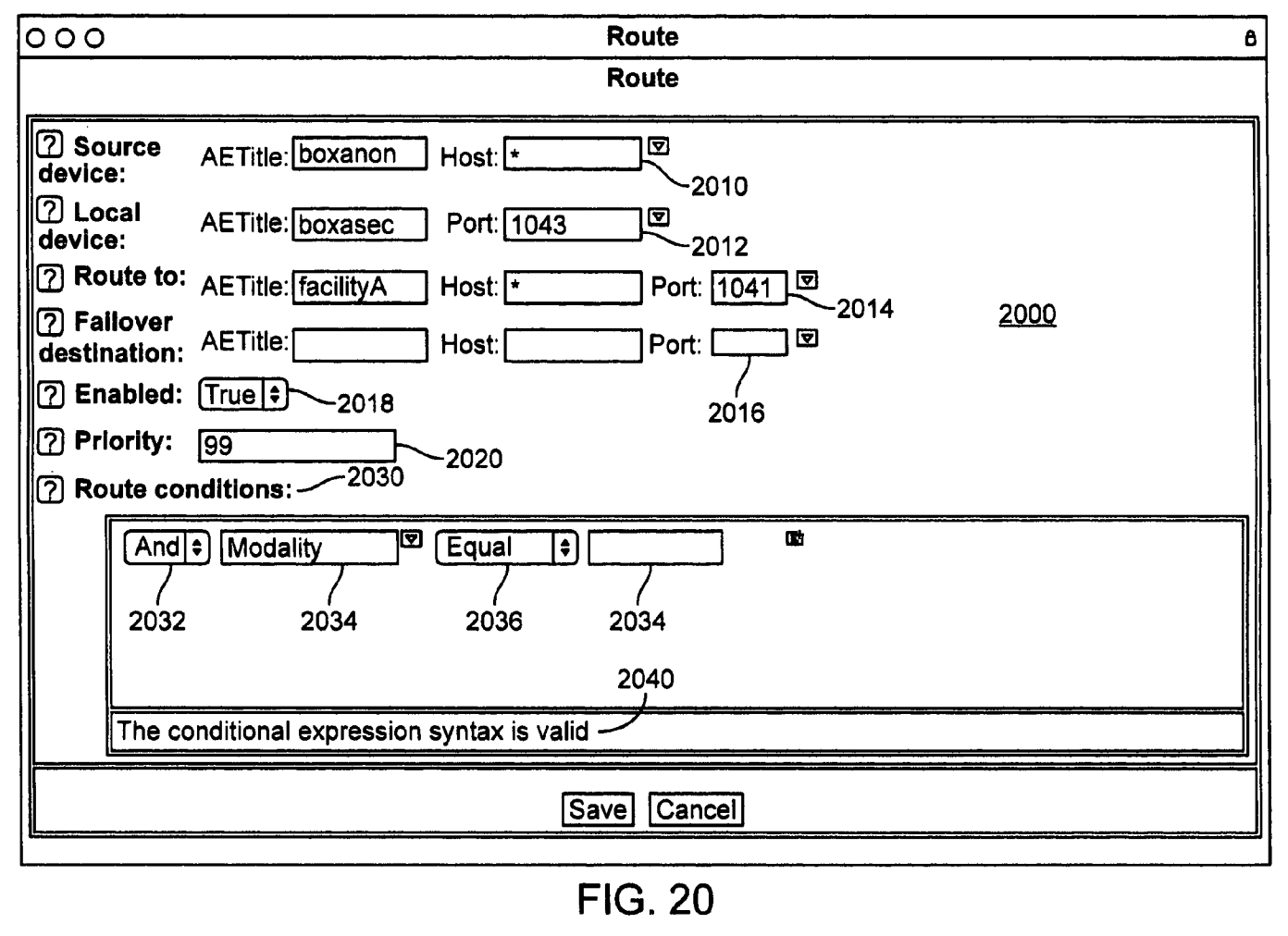

To provide for user configuration and programming of routing conditions 450, a graphical user interface (GUI) 2000 is provided as shown in FIG. 20. The GUI 2000 includes a plurality of user-configurable fields including Source device, Local device, Route to, and Failover destination fields 2010, 2012, 2014 and 2016 respectively. Fields 2010, 2012, 2014 and 2016 are user-configurable to include the application entity title and other information of respective DICOM devices or programs. Routing may be enabled (True) or disabled (False) using the Enabled field 2018. A Priority field 2020 provides for user-configurable prioritization of the routing.

A Route conditions field 2030 provides for user-configurable routing conditions including a logical operator field 2032, operands fields 2034, and the operator field 2036. The radiological data routing sub-engine 400 is operable to provide the user with a confirmation 2040 of the syntax of the routing conditions 2030.

Figure 21:
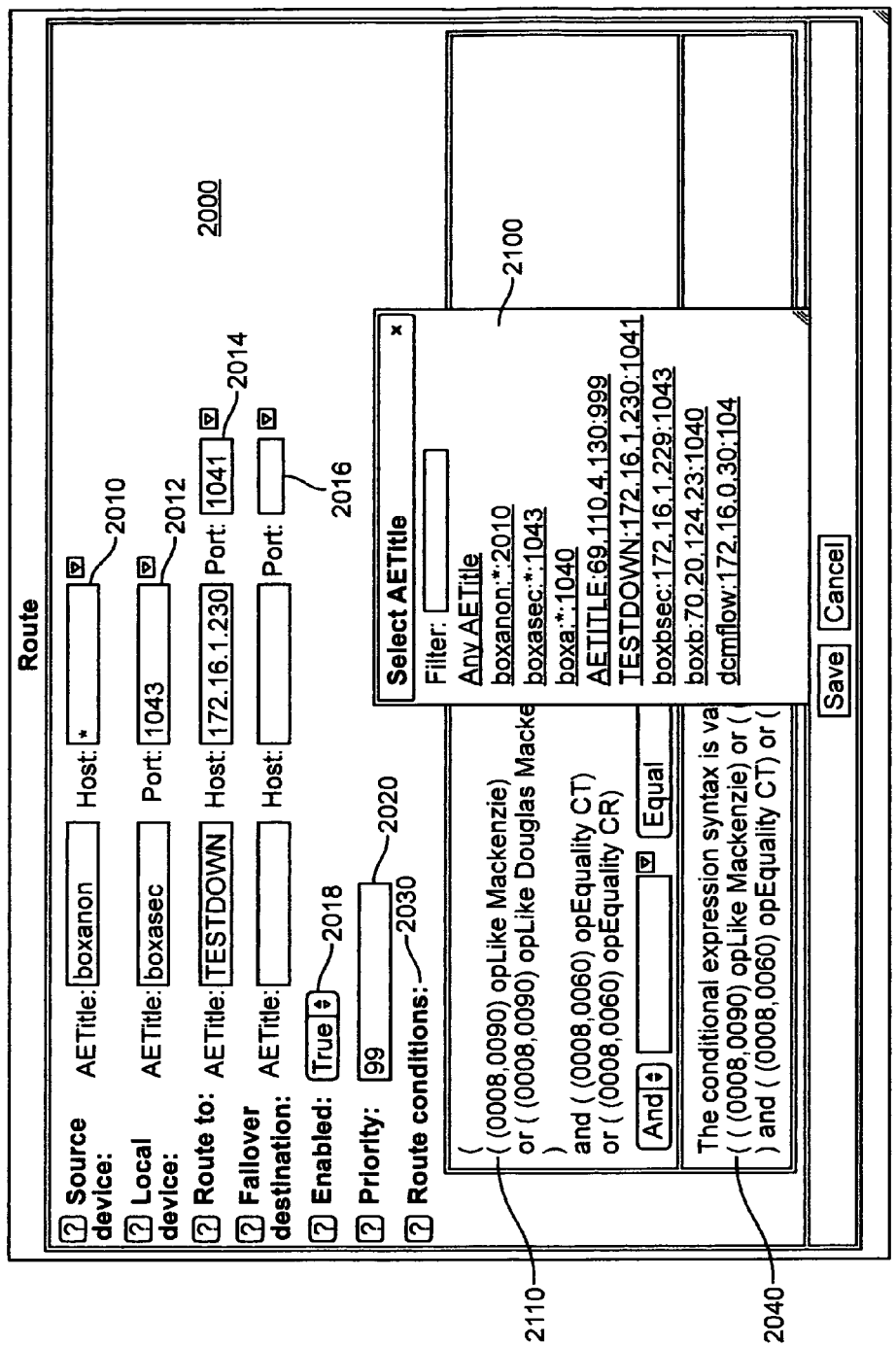
FIG. 21 is screenshot of the graphical user interface of FIG. 20 showing a pop-up box of user-selectable AETitles.
Figure 22:
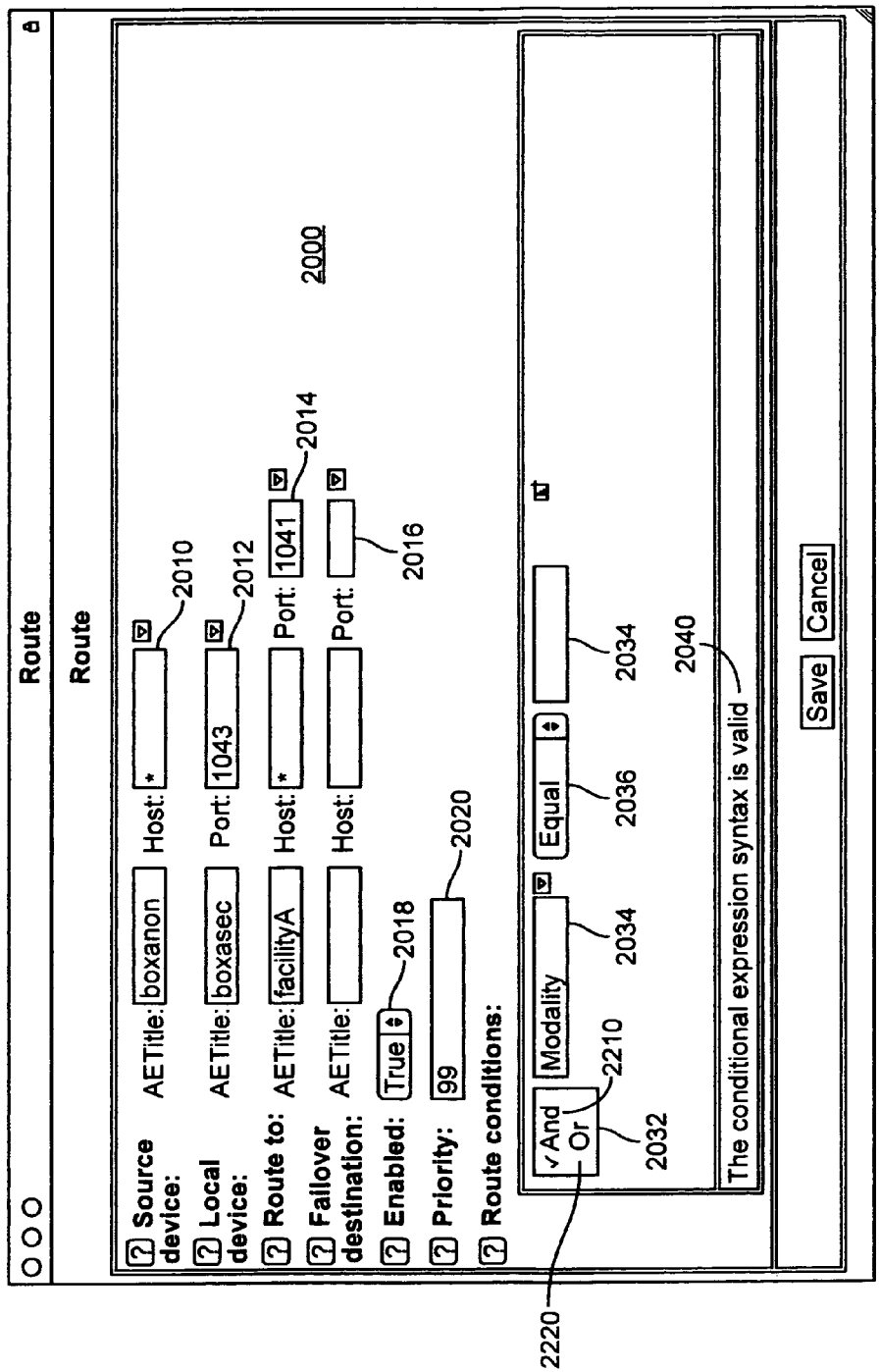
FIG. 22 is a screenshot of the graphical user interface of FIG. 20 showing a pop-up box of user-selectable logical operators.
Figure 23:
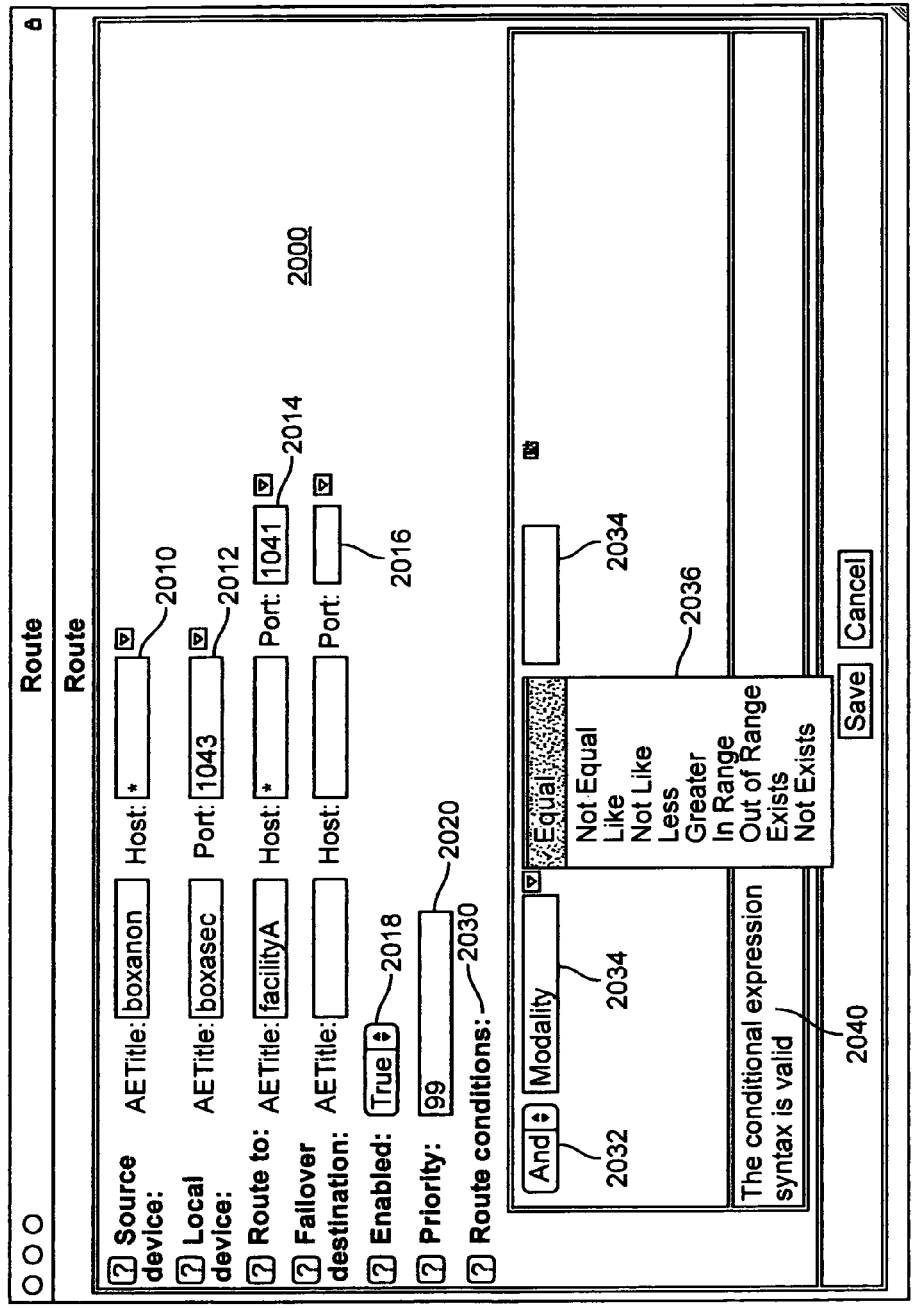
FIG. 23 is a screenshot of the graphical user interface of FIG. 20 showing a pop-up box of user-selectable logical conditions.
Figure 24:
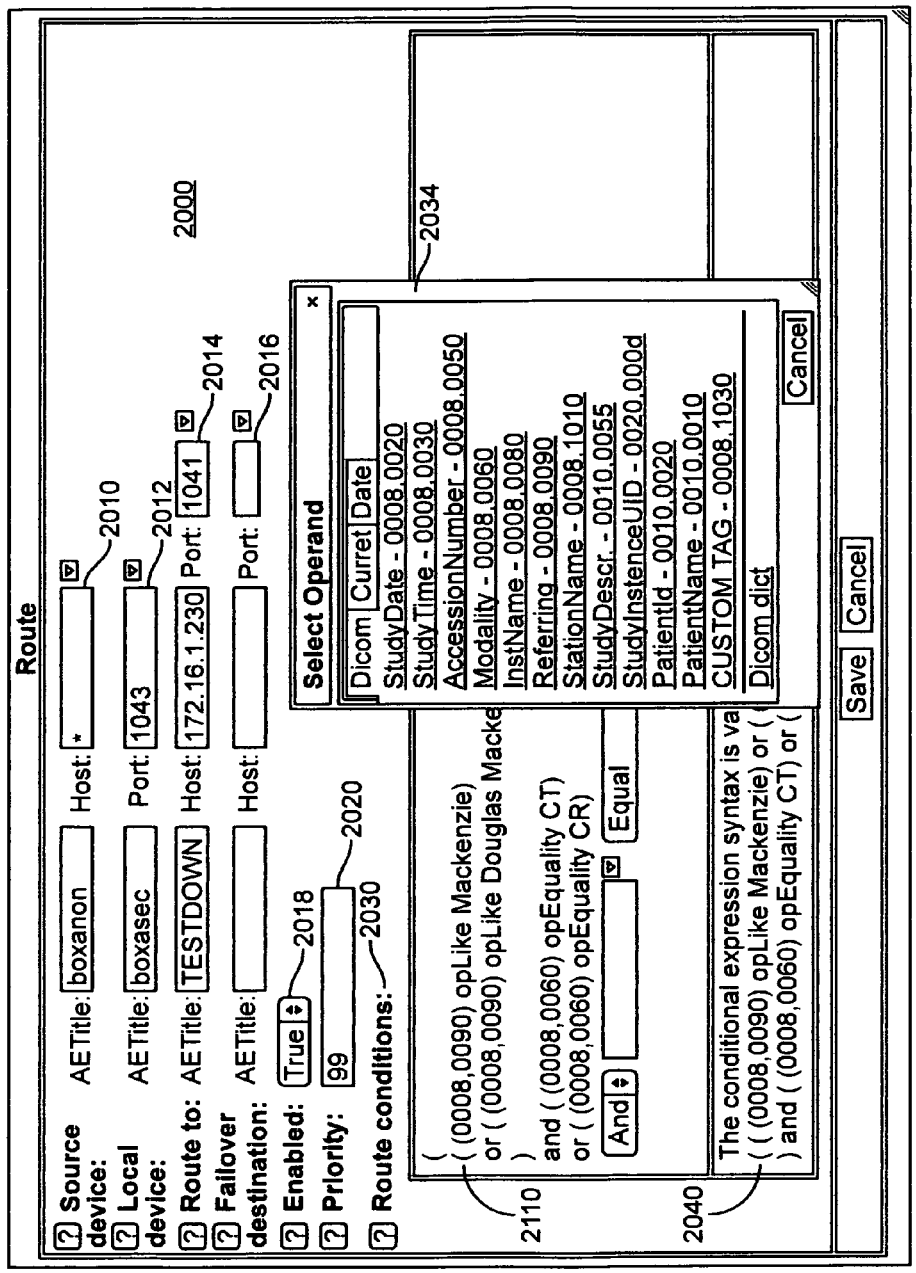
FIG. 24 is a screenshot of the graphical user interface of FIG. 20 showing a pop-up box of user-selectable operands.

With reference to FIG. 21, a pop-up box 2100 is shown from which the user may select the application entity titles of the fields 2010, 2012, 2014 and 2016. FIG. 22 illustrates the logical operator field that includes the logical operators And 2210 and Or 2220. FIG. 23 illustrates the operator field 2036 that includes Equal, Not Equal, Like, Not Like, Less, Greater, In Range, Out of Range, Exists, and Not Exists. FIG. 24 illustrates the user-selectable operands field 2034 that includes DICOM tags StudyDate, StudyTime, AccessionNumber, Modality, InstName, Referring, StationName, StudyDescr, StudyInstanceUID, PatientID, PatientName, and the user-configurable CUSTOM TAG. FIG. 24 also shows an exemplary routing condition 2110 (also shown in FIG. 21).

Figure 5:
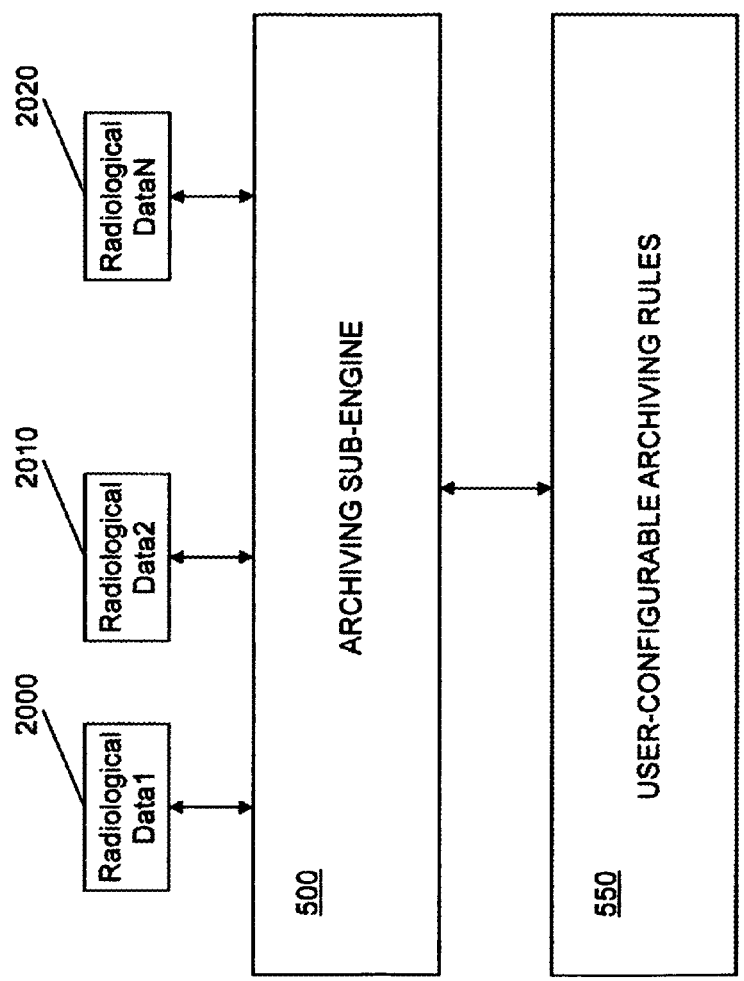
FIG. 5 is a graphical representation of a radiological data archiving sub-engine of the user-configurable radiological data transformation, routing and archiving engine.

A radiological data archiving sub-engine 500 (FIG. 5) uses standard protocols (HL7, DICOM, XML and SNMP) to archive radiological data 2000 (Radiological Data1), 2010 (Radiological Data2) and 2020 (Radiological DataN) (patient studies, for example) from disparate radiology systems (such as RIS server 130, HIS server 140, and EMR server 150). User-configurable rules 550 provide for archiving of the radiological data 2000, 2010 and 2020.

A computer-implemented method 830 (FIG. 8B) in accordance with the invention includes the steps of providing 832 a graphical user to the user, receiving 834 user-configured archiving rules, and processing 836 the user-configured archiving rules in a processor to provide for archiving of patient radiological data.

Figure 26:
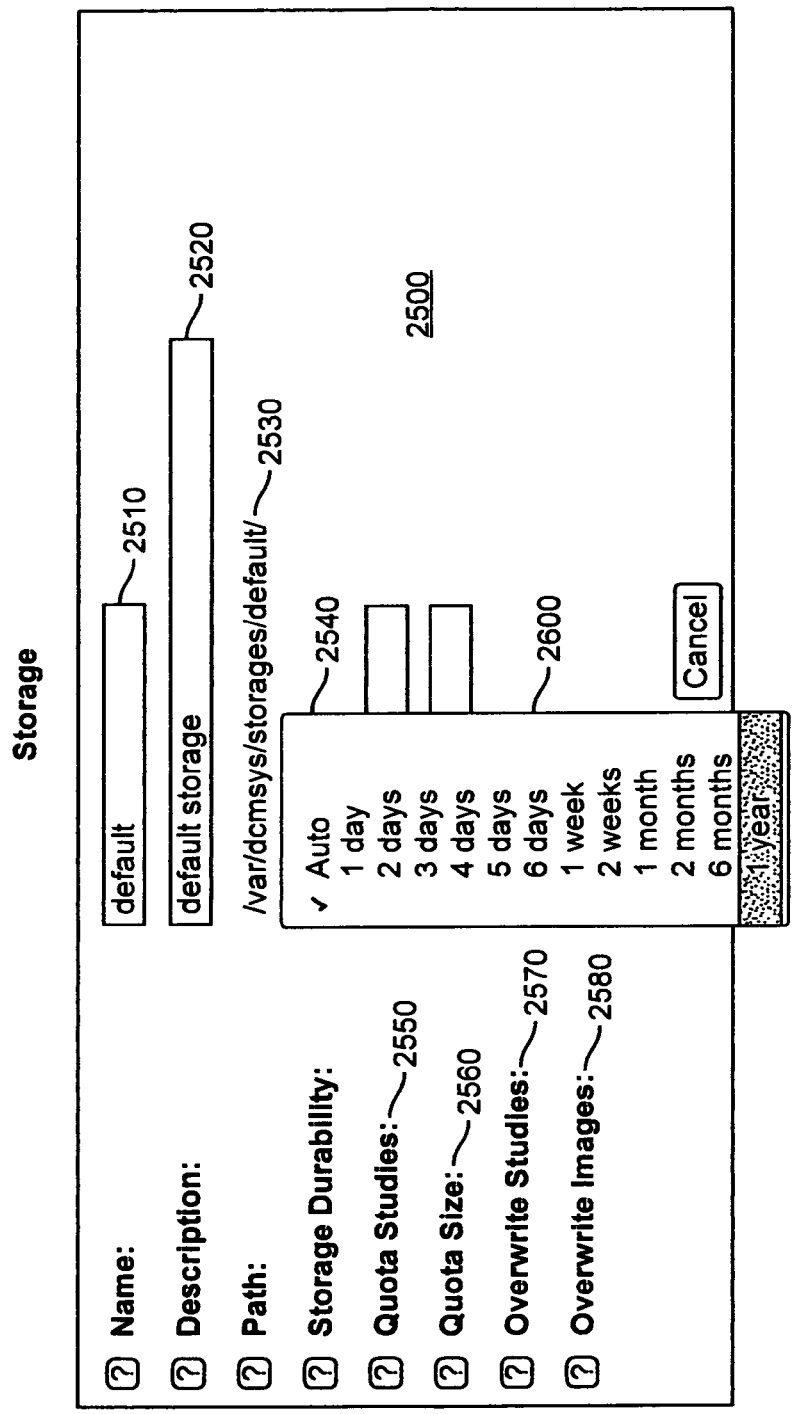
FIG. 26 is a screenshot of the graphical user interface of FIG. 30 showing a pop-up box of user-selectable storage duration.

To provide for user configuration and programming of archiving rules 550, a graphical user interface (GUI) 2500 is provided as shown in FIG. 25. The GUI 2500 includes a plurality of user-configurable fields including Name 2510, Description 2520, Path 2530, Storage Durability 2540, Quota Studies 2550, Quota Size 2560, Overwrite Studies 2570 and Overwrite Images 2580. Storage Durability 2540 provides a pop-up window 2600 (FIG. 26) providing user-selected storage duration. Overwrite Studies 2570 and Overwrite Images 2580 may be selected as either True or False.

Figure 6:
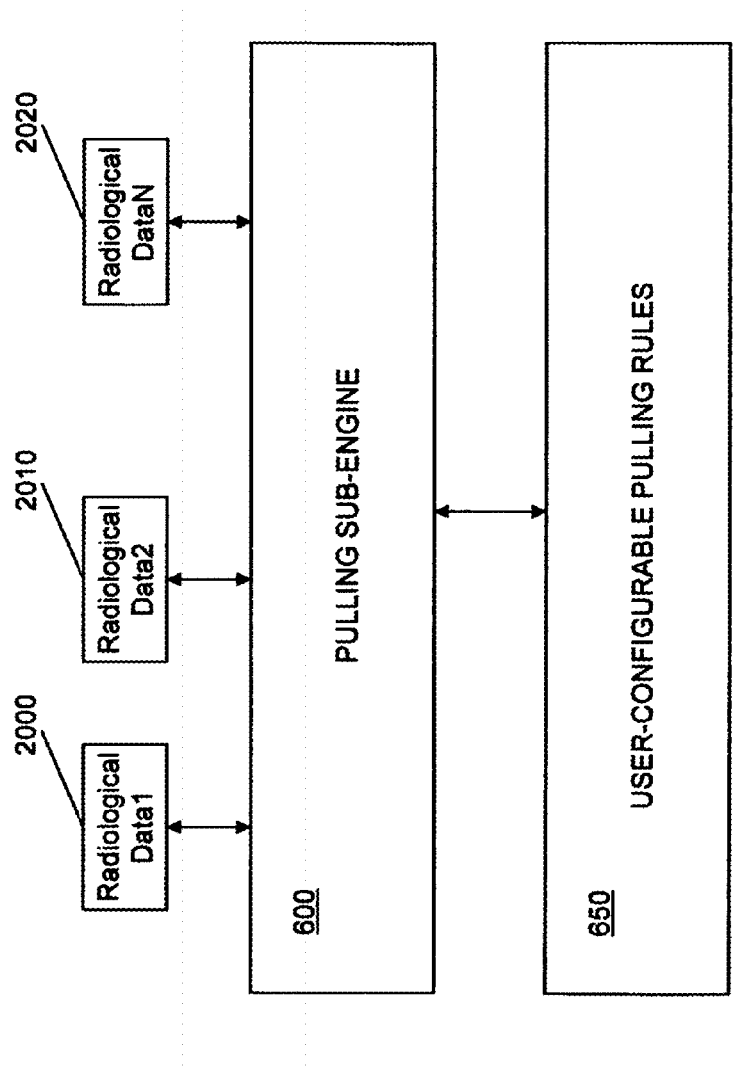
FIG. 6 is a graphical representation of a radiological data pulling sub-engine of the user-configurable radiological data transformation, routing and archiving engine.

A radiological data priors puller sub-engine 600 (FIG. 6) uses standard protocols (HL7, DICOM, XML and SNMP) to pull prior radiological data 2000 (Radiological Data1), 2010 (Radiological Data2) and 2020 (Radiological DataN) (patient studies, for example) from disparate radiology systems (such as RIS server 130, HIS server 140, and EMR server 150). User-configurable puller rules 650 provide for pulling prior radiological data 2000, 2010 and 2020.

A computer-implemented method 820 (FIG. 8A) in accordance with the invention includes the steps of providing 822 a graphical user to the user, receiving 824 user-configured pulling conditions, and processing 826 the user-configured pulling conditions a processor to provide for pulling of prior patient radiological data.

To provide for user configuration and programming of priors puller rules 650, a graphical user interface (GUI) 2700 is provided as shown in FIG. 27. The GUI 2700 includes a plurality of user-configurable fields including Name 2710 and Description 2720. Source device and Local device fields 2730 and 2740 respectively are user-configurable to include the application entity title and other information of respective DICOM devices or programs. Pulling priors may be enabled (True) or disabled (False) using the Enabled field 2750. The type of request is user-configurable using the Request type field 2752 and includes Get and Move functions. A Prior fetch limit field provides the user with a means of selecting the limit of priors fetched.

The destination of the C-Move request is selectable using the C-Move dest AE field 2756.

Figure 29:
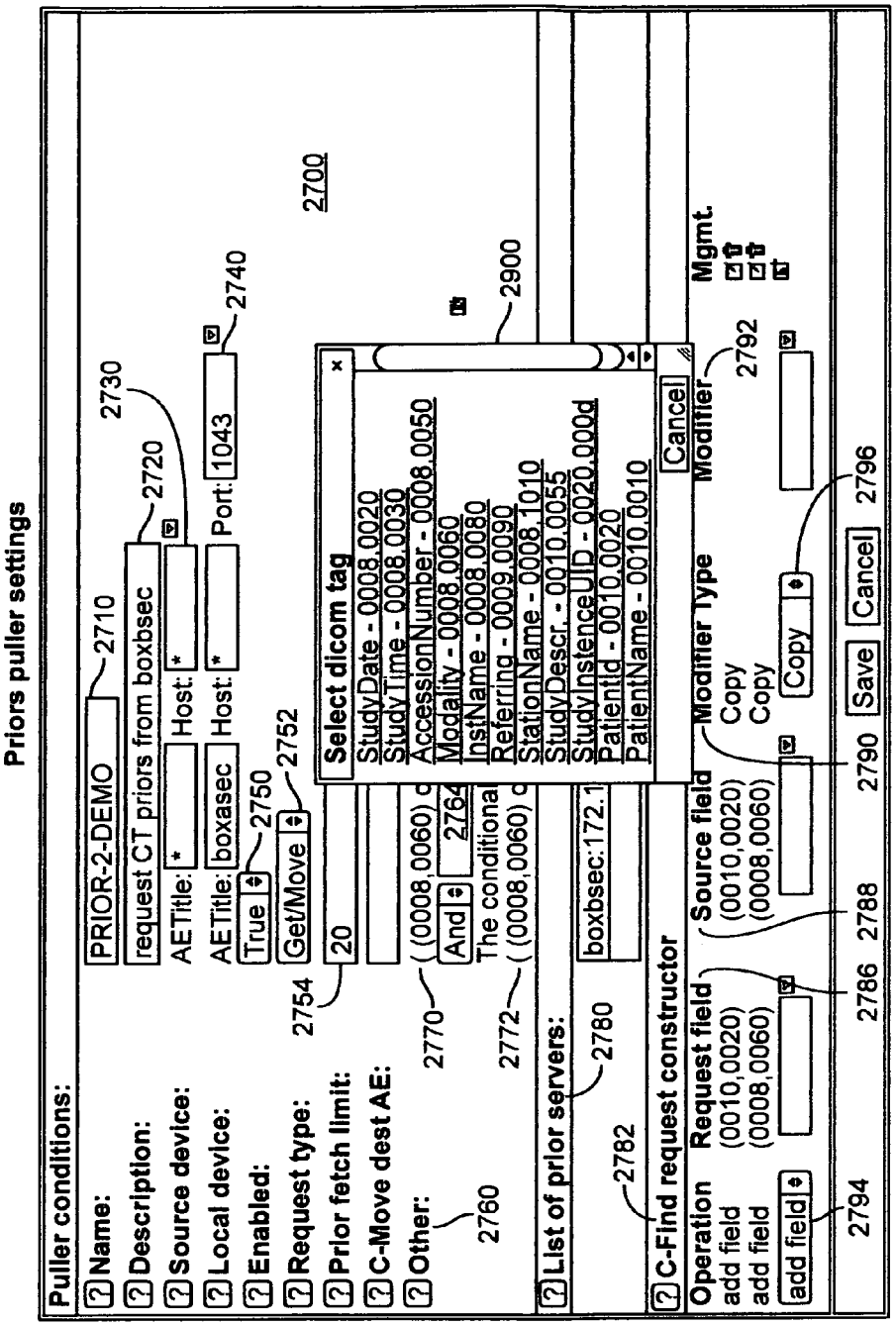
FIG. 29 is a screenshot of the graphical user interface of FIG. 25 showing a pop-up box of user-selectable DICOM tags.
Figure 30:
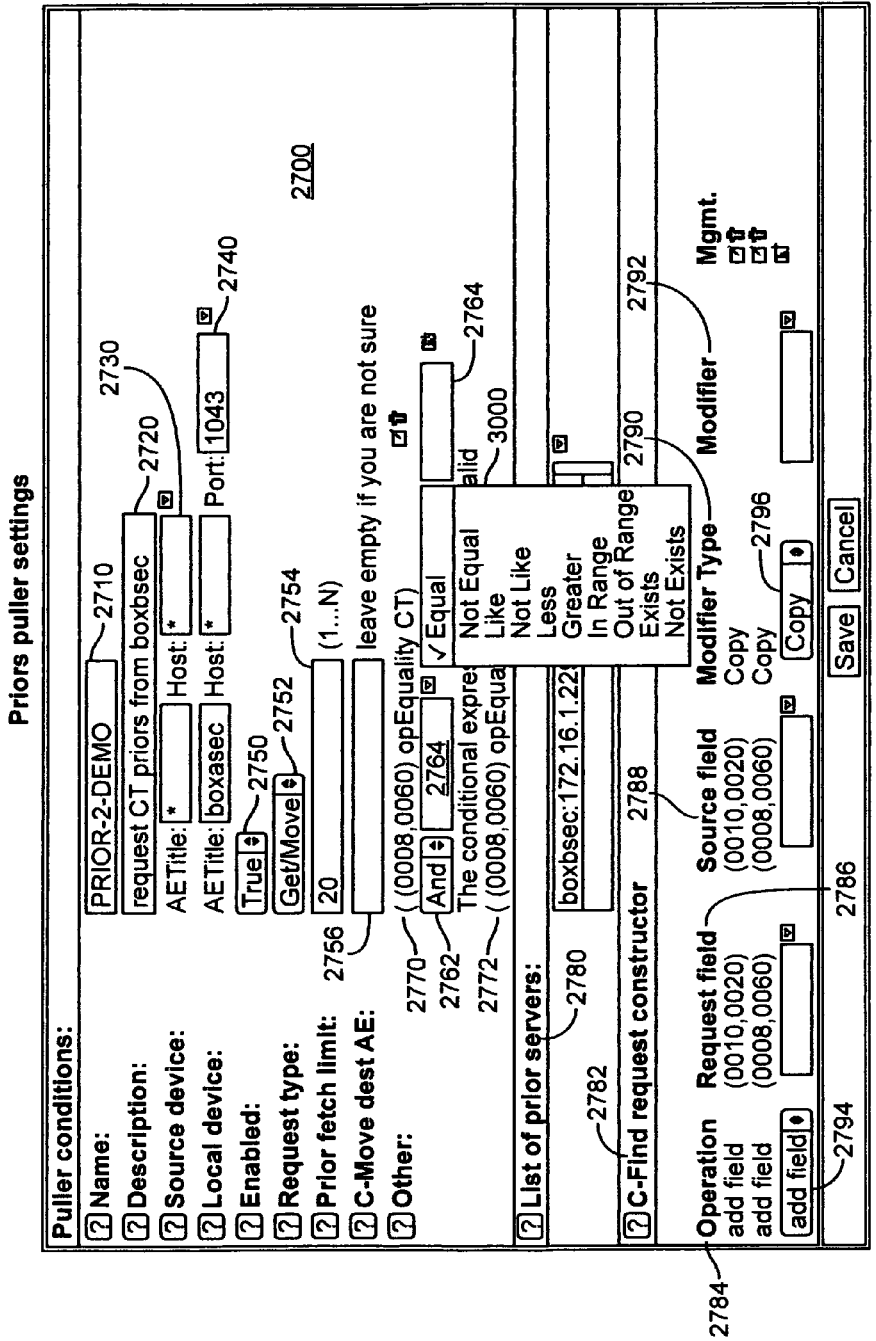
FIG. 30 is a screenshot of the graphical user interface of FIG. 25 showing a pop-up box of user-selectable conditions.

A conditional expression 2770 is user-configurable using the Other field 2760. The logical operator field 2762 (And or Or), the operands fields 2764 and the operator field 2766 provide the user with means for constructing the conditional expression 2770. As shown in FIG. 29, a pop-up box 2900 provides the user with selectable DICOM tags including usercustomizable tags such as the CUSTOM TAG. With reference to FIG. 30, a pop-up box 3000 provides the user with selectable operators including Equal, Not Equal, Like, Not Like, Less, Greater, In Range, Out of Range, Exists and Not Exists. The radiological data priors puller sub-engine 600 is operable to provide the user with a confirmation 2772 of the syntax of the conditional expression 2770.

Figure 28:
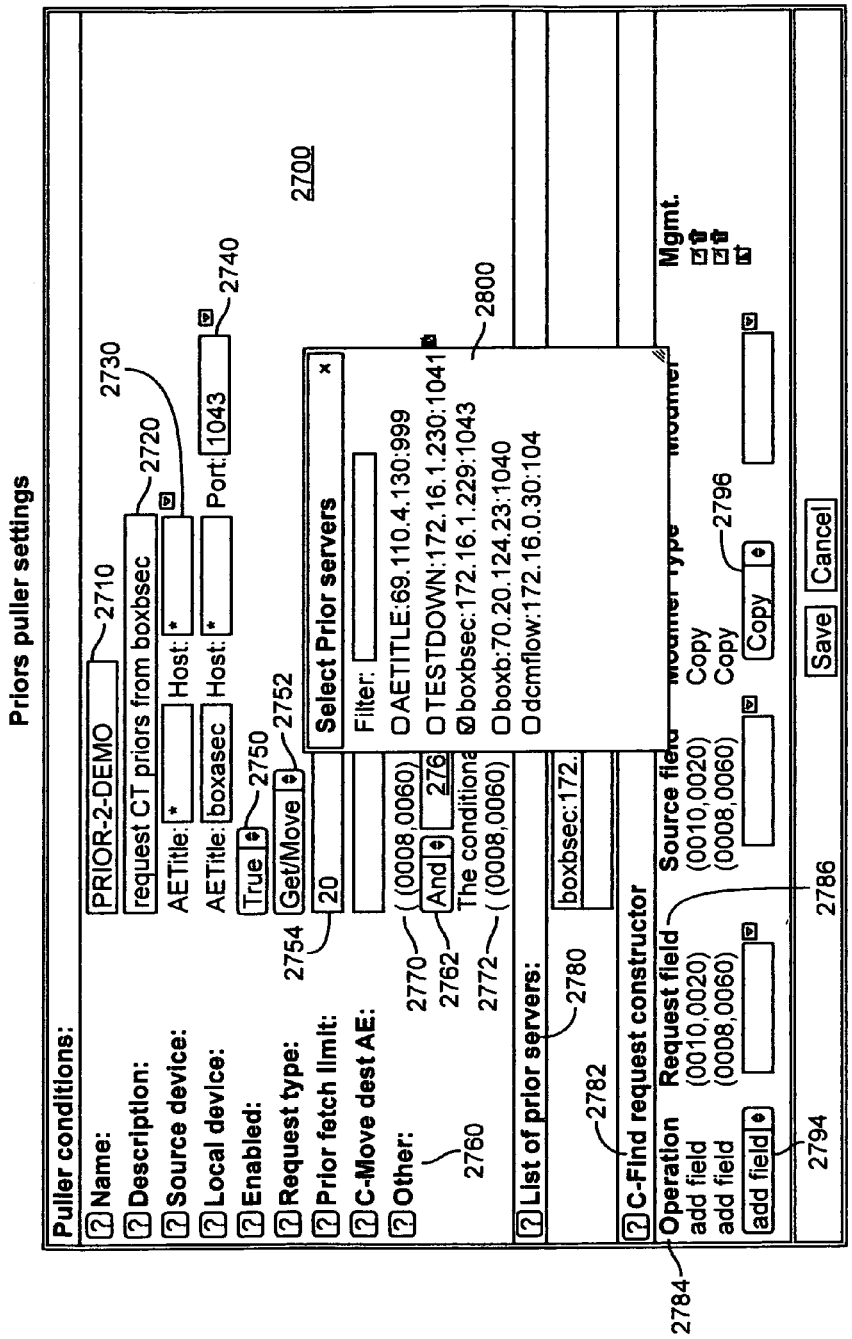
FIG. 28 is a screenshot of the graphical user interface of FIG. 25 showing a pop-up box of user-selectable prior servers.
Figure 31:
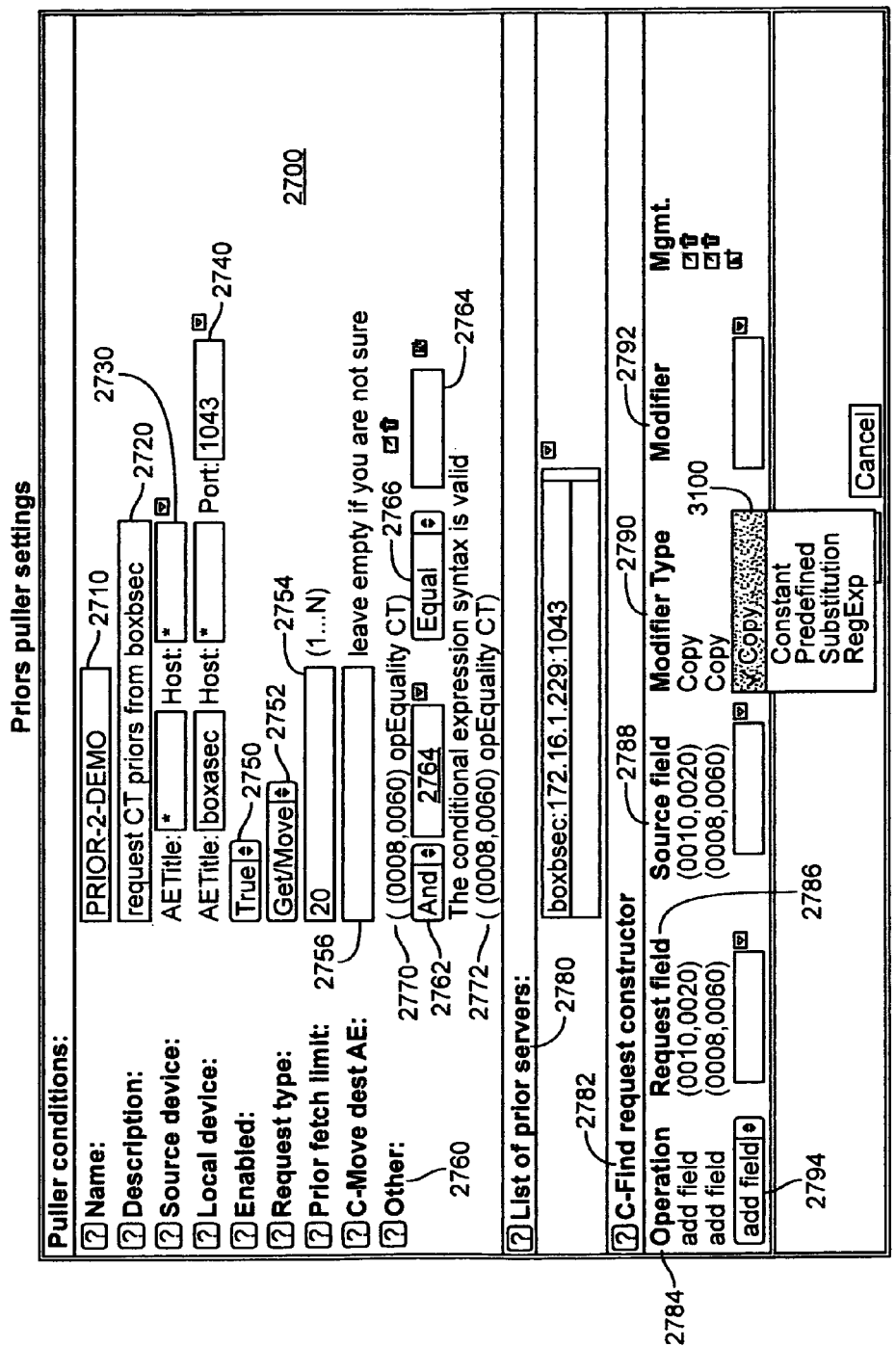
FIG. 31 is a screenshot of the graphical user interface of FIG. 25 showing a pop-up box of user-selectable modifier types.

A List of prior servers field 2780 is user-selectable by means of a pop-up box 2800 (FIG. 28). A C-Find request constructor field 2782 provides the user with configurable fields including an Operation field 2784 having a pop-up box 2794, a Request field 2786, a Source field 2788, a Modifier Type 2790 having a pop-up box 3100 (FIG. 31) and a Modifier field 2792. The Modifier Type pop-up box 3100 provides for user-selectable modifier types including Copy, Constant, Predefined, Substitution and RegExp.

In accordance with an aspect of the invention, the radiological data transformation sub-engine 300, the radiological data routing sub-engine 400, the radiological data archiving sub-engine 500 and the radiological data priors pulling sub-engine 600 can be integrated into an HL7 Workflow.

A computer-implemented method 840 (FIG. 8C) in accordance with the invention includes the steps of providing 842 a graphical user interface to the user, receiving 844 user-configured HL7 workflow events, and processing 846 the user-configured HL7 workflow events in a processor to provide for standardized HL7 workflow.

Figure 32:
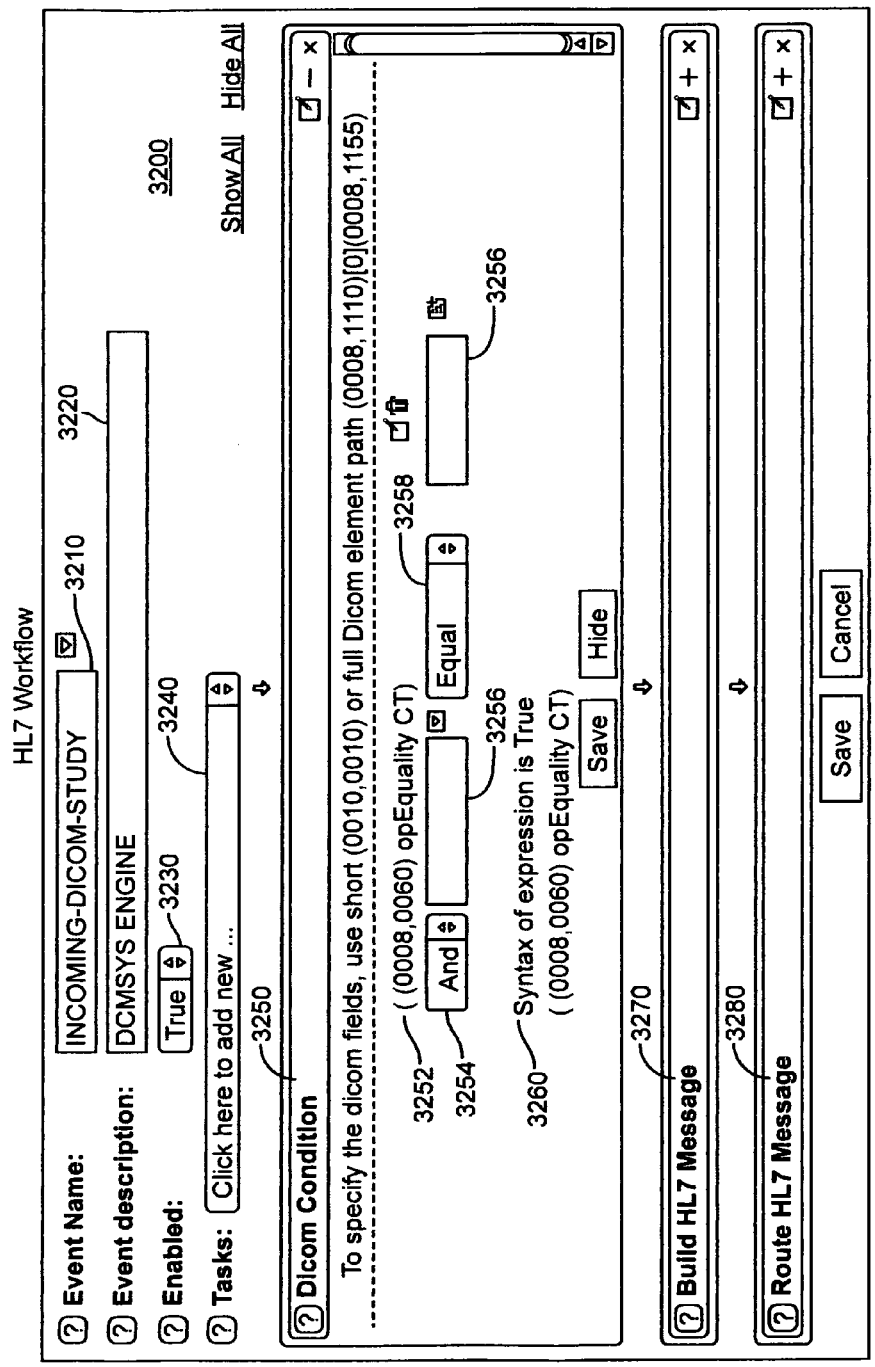
FIG. 32 is a screenshot of a graphical user interface that provides for user-configurable HL7 workflow showing a pop-up box of default events.
Figure 33:
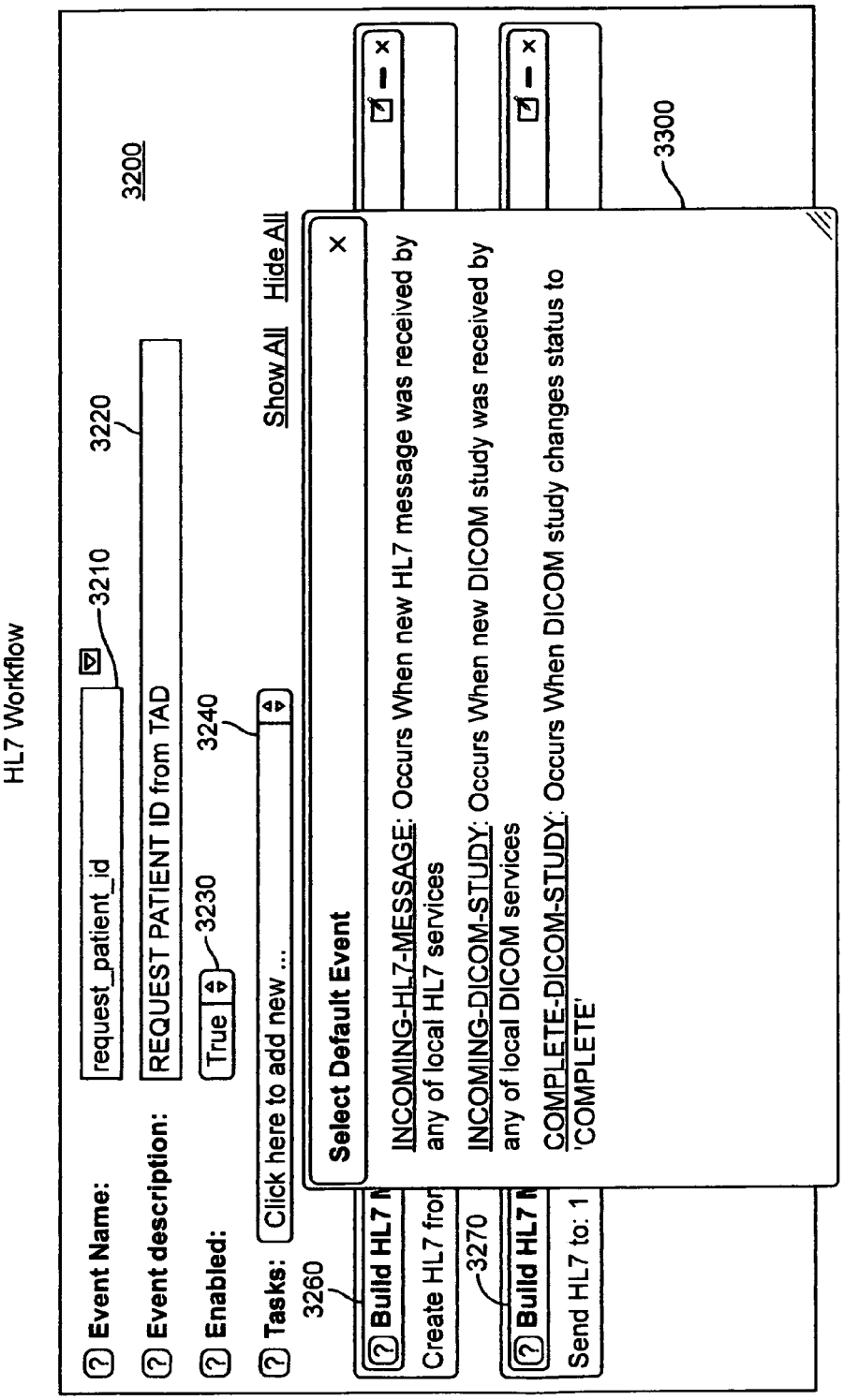
FIG. 33 is a screenshot of the graphical user interface of FIG. 32 showing DICOM conditions.

An HL7 Workflow GUI 3200 is shown in FIG. 32. The GUI 3200 provides for user-configurable events and includes an Event Name field 3210 and an Event description field 3220. A pop-up window 3300 (FIG. 33) provides for user-selectable default events such as INCOMING-HL7-MESSAGE, INCOMING-DICOM-STUDY and COMPLETE-DICOM-STUDY. The HL7 workflow may be enabled (True) or disabled (False) using the Enabled field 3230. A Dicom condition includes user-configurable fields including a logical operator field 3254 (And and Or), operand fields 3256 and an operator field 3258. For ease of use, the user is provided a confirmation 3260 of the syntax of the Dicom condition.

Figure 34:
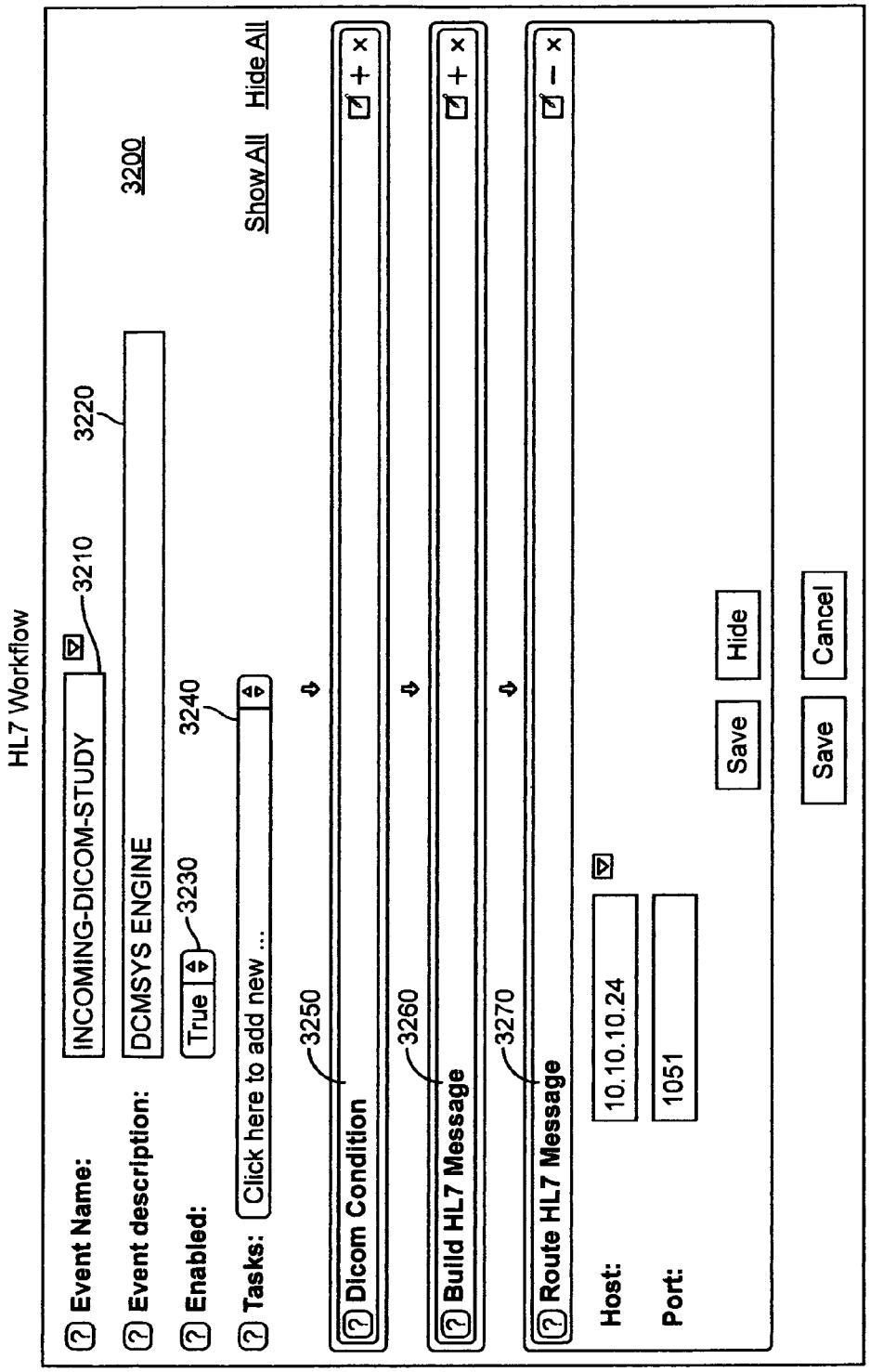
FIG. 34 is a screenshot of the graphical user interface of FIG. 32 showing an HL7 message.
Figure 36:
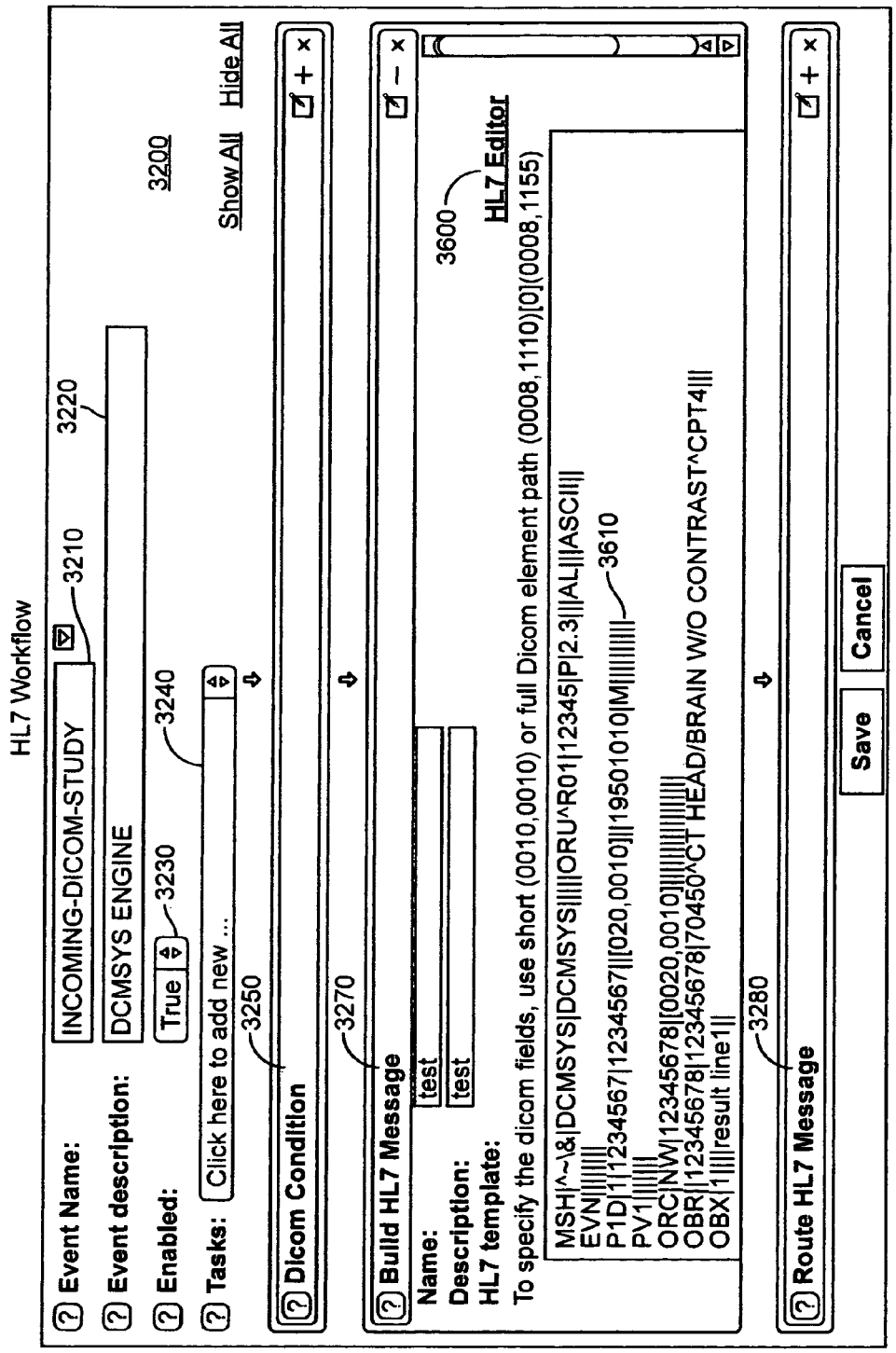
FIG. 36 is a screenshot of the graphical user interface of FIG. 32 showing a pop-up box of user-selectable tasks.
Figure 37:
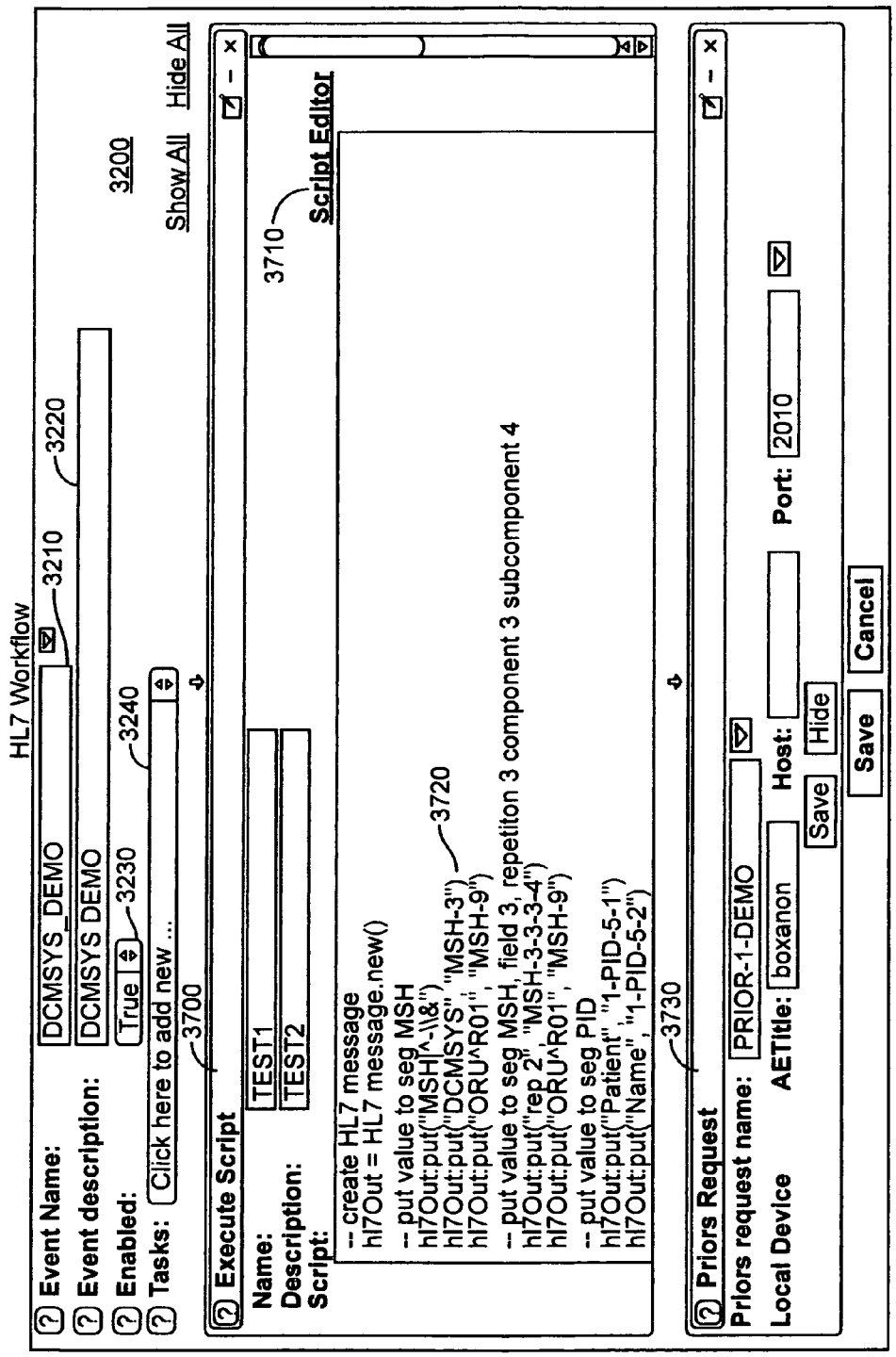
FIG. 37 is a screenshot of the graphical user interface of FIG. 32 showing a script editor.

A Tasks field 3240 includes a pop-up window 3500 (FIG. 35) from which the user may select from HL7 Condition, HL7 Transformation, Route HL7 Message, Send HL7 Message, Build Worklist entry, Exort to CSV file, Build HL7 Message, Return HL7 result, Priors Request, Submit document to the XDS Repository Service, Execute script, Build Dicom object and Dicom Condition. As shown in FIG. 34, the Dicom Condition 3250, the Build HL7 Message 3260 and the Route HL7 Message 3270 tasks are selected and comprise the event "DCMSYS ENGINE". The event "DCMSYS ENGINE" also includes the HL7 Message 3270 as shown in FIG. 37. The script 3260 of the HL7 Message 3270 may be written using the HL7 Editor 3600.

With reference to FIG. 37, the event "DCMSYS DEMO" is shown and includes an Execute script event 3700 comprising the script 3720 and a Priors request 3730. The Priors request references the PRIOR-1-DEMO. The event "DCMSYS DEMO" comprises the source value 946 of the exemplary DICOM Transformation shown in FIG. 19.

With reference to FIG. 37, the event "DCMSYS DEMO" is shown and includes an Execute script event 3700 comprising the script 3720 and a Priors request 3730. The Priors request references the PRIOR-1-DEMO. The event "DCMSYS DEMO" comprises the source value 946 of the exemplary DICOM Transformation shown in FIG. 19.

A computer-implemented method 850 (FIG. 8D) in accordance with the invention includes the steps of providing 852 a graphical user interface to the user, receiving 854 a user-configured encryption scheme, and processing 856 the user-configured encryption scheme in a processor to provide for secure connection between devices.

Figure 39:
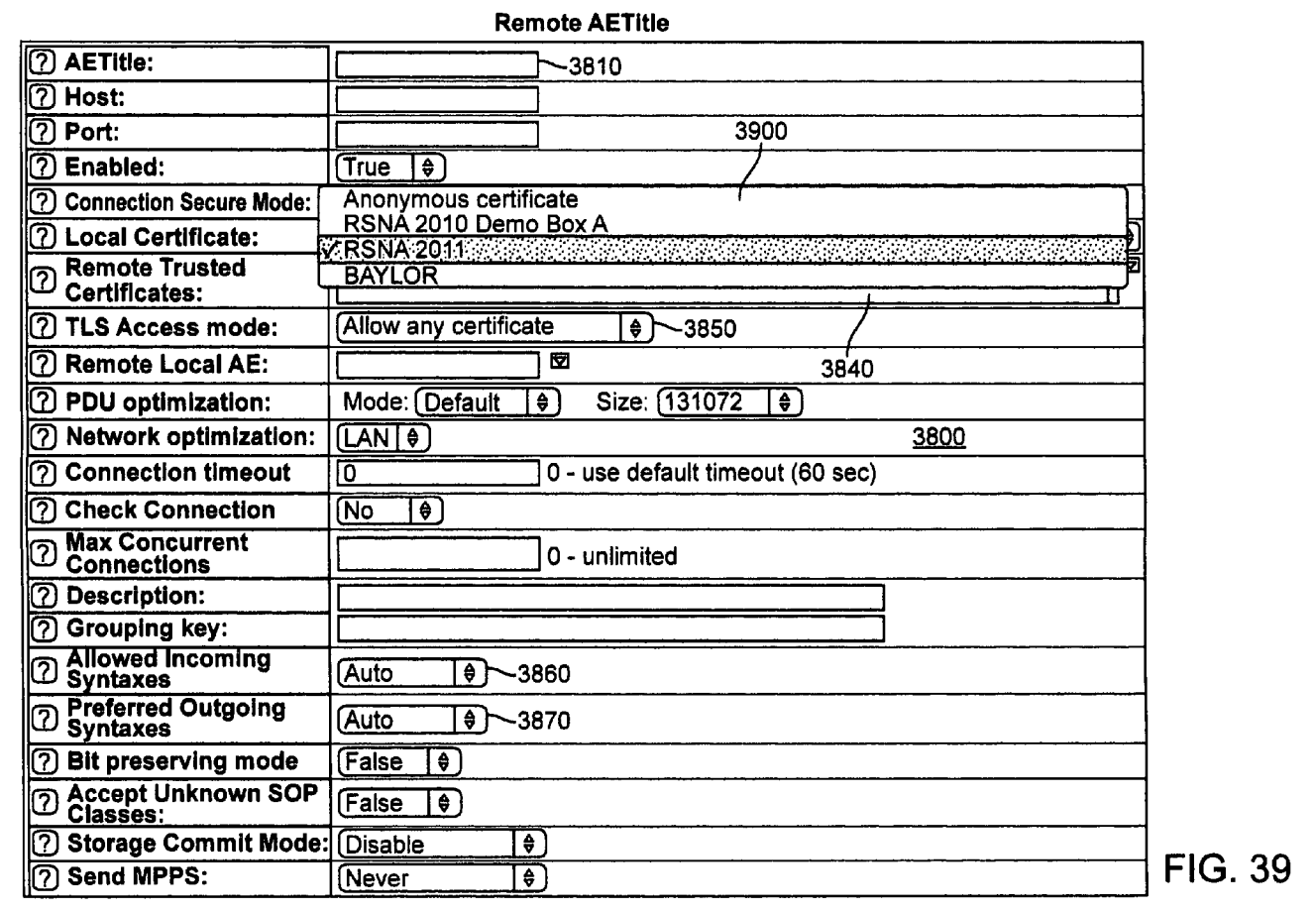
Figure 40:
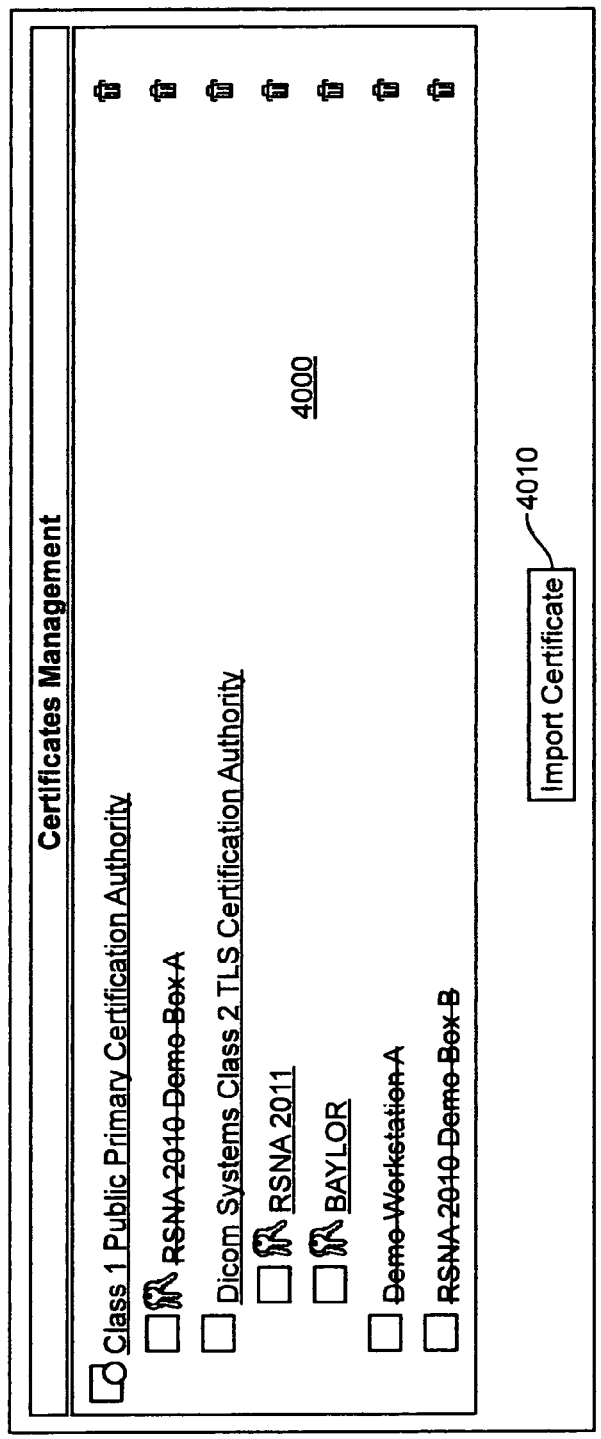
FIG. 40 is a screenshot of a graphical user interface that provides for user-configurable certificate management.
Figure 41:
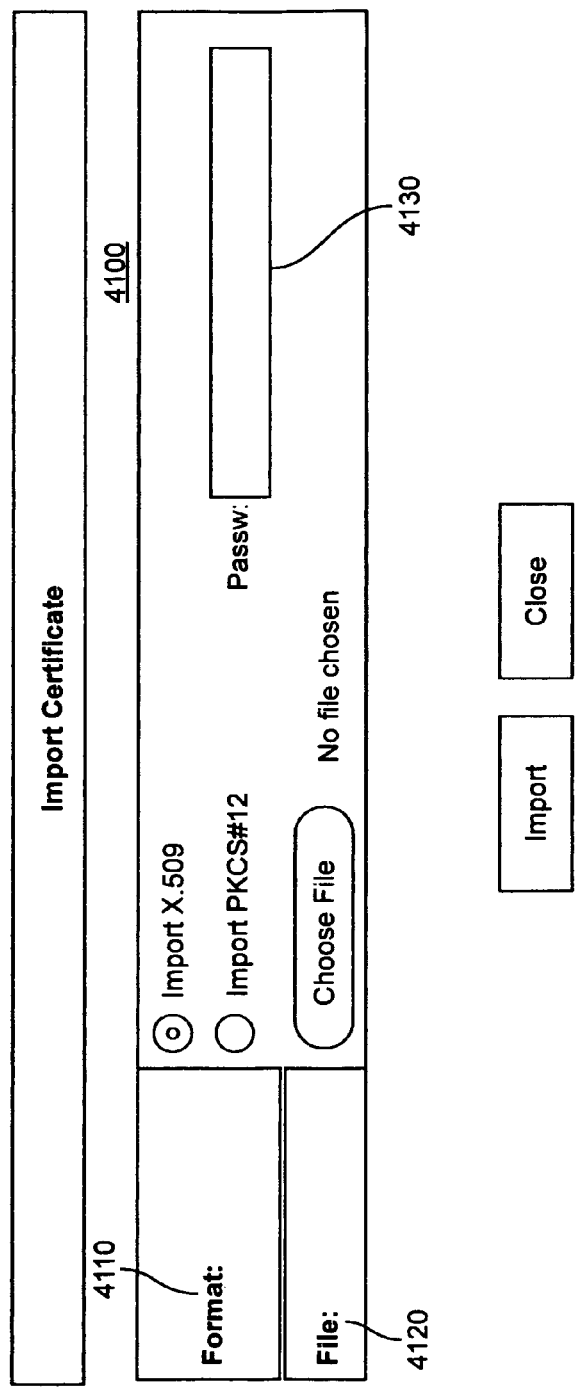
FIG. 41 is a screenshot of a graphical user that provides for user-configurable certificate importation.

To provide for user configuration and programming of the encryption scheme, a graphical user interface (GUI) 3800 is provided as shown in FIG. 38. In configuring the remote AETitle 3810, for example, a connection secure mode 3820 may be set to either Nonsecure or Secure. A local certificate 3830 and a remote trusted certificate 3840 may be selected from a pop-up window 3900 (FIG. 39). Certificate management is provided by means of a graphical user interface 4000 (FIG. 40) that includes an "Import certificate" button 4010. Certificates may be imported to the GUI 4000 and to the pop-up window 3900 by user access to the "Import Certificate" graphical user interface 4100 (FIG. 41). The format 4110 of the certificate, a password 4130 and the certificate file 4120 may be selected by means of the GUI 4100.

A computer-implemented method 860 (FIG. 8E) in accordance with the invention includes the steps of providing 862 a graphical user interface to the user, receiving 864 a user-configured compression scheme, and processing 866 the user-configured compression scheme in a processor to provide for compression of patient radiological data.

With reference to FIG. 38, allowed incoming syntaxes 3860 and preferred outgoing syntaxes 3870 (compression schemes) are user-configurable. Transfer syntaxes selectable by the user are shown in the graphical user interfaces 4200 of FIG. 42, FIG. 43, FIG. 44 and FIG. 45.

The user-configurable radiological data transformation, routing and archiving engine in accordance with the invention provides a web-based software tool configured to run on a server or virtual base server. Users do not need to be programmers in order to write the described rules, conditions and events as the graphical user interfaces are intuitive and easy to use. The user-configurable radiological data transformation, routing and archiving engine also provides a versatile tool that provides a user with the means for transforming, routing, archiving, pulling, encrypting and compressing patient radiological data, creating worklists and managing workflow. The user-configurable radiological data transformation, routing and archiving engine further provides for the integration of the output of diverse devices in a single engine.

I claim:

1. A user-configurable medical data filtering, transformation, routing and archiving engine comprising:
    a network interface coupled to a plurality of medical data capturing systems;
    a medical data processing device coupled to a memory, the processing device being programmed to perform the steps of:
        displaying a user interface, the user interface enabling a set of medical data filter condition, a set of medical data transformation rules, a set of routing rules, and a set of archiving rules;
            wherein the set of medical data filter conditions comprises a first logical operator and any of a first DICOM field, a first HL7 field, a first XDS-I information field; and
            the set of medical data transformation rules comprises a transformation filter condition, the transformation filter condition comprising a first logical operator and any of a first DICOM field, a first HL7 field, and a first XDS-I information field;
        receiving, through the user interface, the set of medical data filter conditions, the set of medical data transformation rules, the set of routing rules, and the set of archiving rules;

obtaining a first medical data set from the plurality of medical data capturing systems by applying the set of medical data filter conditions to the medical data capturing system;

receiving through the user interface a user-configurable workflow task;

applying the user-configurable workflow task to the first medical data set;

modifying the first medical data set in accordance with the user-configurable workflow task;

modifying the first medical data set in accordance with the set of medical data transformation rules when the transformation filter condition is satisfied; and obtaining a second medical data set comprising applied a modified first medical data set.

2. The engine of claim 1, wherein the medical data processing device is programmed to receive a user-configurable encryption scheme and a user-configurable compression scheme through the user interface and to modify medical data in accordance with the encryption scheme and the user-configurable compression scheme.

3. The engine of claim 1, wherein set of medical data transformation rules further comprises an operation selected from the group consisting of: modify field, remove field and run script.

4. The engine of claim 1, wherein the medical data processing device is further programmed to perform the step of: receiving, through the user interface, priors pulling conditions, the priors pulling conditions comprising a second logical operator any of the first DICOM field, a second DICOM field, the first HL7 field, a second HL7 field, the first XDS-I information field, and a second XDS-I information field.

5. The engine of claim 1, wherein the user-configurable HL7 workflow further comprises a task selected from the group consisting of HL7 condition, HL7 transformation, route HL7 message, send HL7 message, build worklist entry, export to CSV file, build HL7 message, return HL7 message, priors request, submit document to the XDS repository service, execute script, build DICOM object and DICOM condition.

6. A computer-implemented method of filtering, transformation, routing and archiving radiological data comprising:

providing, from a medical data processing device coupled to a memory, a graphical user interface (GUI) coupled to a plurality of medical data capturing systems, the GUI enabling configuration of a set of medical data filter conditions, a set of medical data transformation rules, a set of routing conditions, a set of routing rules, a set of prior pulling conditions, a set of prior pulling rules, a set of archiving conditions, and a set of archiving rules;

wherein the set of medical data filter conditions comprises a first logical operator and any of a first DICOM field, a first HL7 field, a first XDS-I information field; and the set of medical data transformation rules comprises a user-configurable script configured to cause the medical data processing device to modify a set of medical data in accordance with a set of predetermined modification parameters;

receiving, at the medical data processing device, the set of medical data filter conditions, the set of medical data transformation rules, the set of predetermined modification parameters, the set of routing conditions, the set of routing rules, the set of prior pulling conditions, the set of prior pulling rules, the set of archiving conditions, and the set of archiving rules;

obtaining a first medical data set from the plurality of medical data capturing systems;

executing, with the medical data processing device, the user configurable script when the set of medical data filter conditions are satisfied;

receiving through the user interface a user-configurable workflow task;

applying the user-configurable workflow task to the first medical data set;

modifying the first medical data set in accordance with the user-configurable workflow task;

modifying the first medical data set in accordance with the set of medical data transformation rules when the transformation filter condition is satisfied; and obtaining a second medical data set comprising applied a modified first medical data set.

7. The computer-implemented method of claim 6, further comprising receiving, at the medical data processing device, a user-configurable encryption scheme and a user-configurable compression scheme.

8. The computer-implemented method of claim 6, wherein, the set of routing rules comprises a second logical operator and any of the first DICOM field, a second DICOM field, the first HL7 field, a second HL7 field, the first XDS-I information field, and a second XDS-I information field.

9. The computer-implemented method of claim 6, wherein the set of priors pulling conditions comprises a second logical operator and any of the first DICOM field, a second DICOM field, the first HL7 field, a second HL7 field, the first XDS-I information field, and a second XDS-I information field.

10. The computer-implemented method of claim 6, wherein the set of archiving rules comprises user-configurable storage duration.

11. The engine of claim 1, wherein:

the set of routing rules comprises a routing condition, the routing condition comprising a second logical operator and any of the first DICOM field, a second DICOM field tags, the first HL7 field, a second HL7 field, the first XDS-I information filed, and a second XDS-I information field; and the medical data processing device is further configured to perform the step of routing the medical data in accordance with the set of routing rules if the routing filter condition is satisfied.

12. The engine of claim 1, wherein:

the set of archiving rules comprises an archiving condition, the archiving condition comprising a second logical operator and any of the first DICOM field, a second DICOM field, the first HL7 field, a second HL7 field, a third HL7 field, the first XDS-I information field, and a second XDS-I information field; and the medical data processing device is further configured to perform the step of archiving the medical data in accordance with the set of archiving rules if the archiving filter condition is satisfied.

* * * * *